(12) United States Patent
Peukert et al.

(10) Patent No.: US 6,924,392 B2
(45) Date of Patent: Aug. 2, 2005

(54) ORTHO, META-SUBSTITUTED BISARYL COMPOUNDS, PROCESSES FOR THEIR PREPARATION, THEIR USE AS MEDICAMENTS, AND PHARMACEUTICAL PREPARATIONS COMPRISING THEM

(75) Inventors: Stefan Peukert, Frankfurt am Main (DE); Joachim Brendel, Bad Vilbel (DE); Horst Hemmerle, Bad Soden (DE); Heinz-Werner Kleemann, Bischofsheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/453,646

(22) Filed: Jun. 4, 2003

(65) Prior Publication Data
US 2003/0225099 A1 Dec. 4, 2003

Related U.S. Application Data

(62) Division of application No. 09/995,771, filed on Nov. 29, 2001, now Pat. No. 6,605,625.

(30) Foreign Application Priority Data

Nov. 30, 2000 (DE) .......................... 100 59 418

(51) Int. Cl.[7] ..................... C07C 233/05; C07C 233/65; A61K 31/16
(52) U.S. Cl. ................. 564/155; 564/158; 560/27; 514/478; 514/616
(58) Field of Search ............... 564/155, 158; 560/27; 514/478, 616

(56) References Cited

U.S. PATENT DOCUMENTS 6,043,284 A * 3/2000 Arrowsmith et al. ....... 514/621
6,703,379 B2 * 3/2004 Iino et al. .................. 514/150

FOREIGN PATENT DOCUMENTS

| WO | WO 9606079 A1 * | 2/1996 |
|----|----|----|
| WO | WO 96/25936 | 8/1996 |
| WO | WO 98/04521 | 2/1998 |
| WO | WO 98/18475 | 5/1998 |
| WO | WO 98/18476 | 5/1998 |
| WO | WO 99/37607 | 7/1999 |
| WO | WO 00/12077 | 3/2000 |

* cited by examiner

*Primary Examiner*—Shailendra Kumar
(74) *Attorney, Agent, or Firm*—Joseph D. Rossi

(57) ABSTRACT

Ortho, meta-substituted bisaryl compounds, processes for their preparation, their use as medicaments, and pharmaceutical preparations including their use as antiarrhythmic active compounds, for example, for the treatment and prophylaxis of atrial arrhythmias, e.g. atrial fibrillation (AF) or atrial flutters. Compounds of the invention include compounds of the formula I

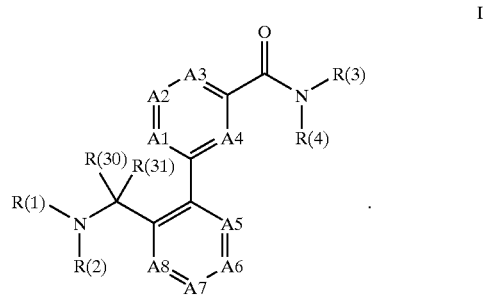

13 Claims, No Drawings

ORTHO, META-SUBSTITUTED BISARYL COMPOUNDS, PROCESSES FOR THEIR PREPARATION, THEIR USE AS MEDICAMENTS, AND PHARMACEUTICAL PREPARATIONS COMPRISING THEM

This application is a DIV of Ser. No. 09/995,771, filed Nov. 29, 2001, now U.S. Pat. No. 6,605,625.

This application claims the benefit of foreign priority under 35 U.S.C. §119 of German patent application no. 10059418.2-44, filed on Nov. 30, 2000 the contents of which are incorporated by reference herein.

The present invention relates to ortho, meta-substituted bisaryl compounds. Embodiments of the invention include, processes for their preparation, their use as medicaments, and pharmaceutical preparations comprising them.

The present invention relates to ortho, meta-substituted bisaryl compounds of the formula I,

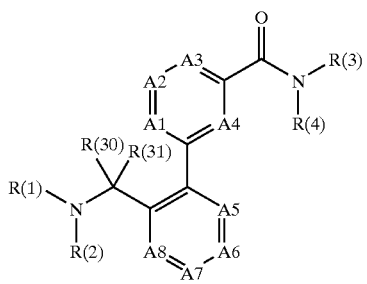

in which:

A1, A2, A3, A4, A5, A6, A7 and A8
  independently of one another are chosen from nitrogen, CH and CR(5), at least four of these groups being CH;
R(1) is C(O)OR(9), SO$_2$R(10), COR(11), C(O)NR(12)R(13) or C(S)NR(12)R(13);
  wherein R(9), R(10), R(11) and R(12)
    independently of one another are chosen from C$_x$H$_{2x}$—R(14);
    where x is 0, 1, 2, 3 or 4, and
    x cannot be 0 if R(14) is OR(15) or SO$_2$Me;
    R(14) is alkyl having 1, 2, 3, 4, 5 or 6 atoms, cycloalkyl having 3, 4, 5, 6, 7, 8, 9, 10 or 11 carbon atoms, CF$_3$, C$_2$F$_5$, C$_3$F$_7$, CH$_2$F, CHF$_2$, OR(15), SO$_2$Me, substituted or unsubstituted phenyl, substituted or unsubstituted naphthyl, substituted or unsubstituted biphenylyl, substituted or unsubstituted furyl, substituted or unsubstituted thienyl or a substituted or unsubstituted N-containing heteroaromatic having 1, 2, 3, 4, 5, 6, 7, 8 or 9 carbon atoms,
      where the substituted phenyl, substituted naphthyl, substituted biphenylyl, substituted furyl, substituted thienyl and the substituted N-containing heteroaromatic are each independently substituted by 1, 2 or 3 substituents chosen from F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
    R(15) is alkyl having 1, 2, 3, 4 or 5 carbon atoms, cycloalkyl having 3, 4, 5 or 6 carbon atoms, CF$_3$, substituted phenyl or unsubstituted phenyl,
      wherein the substituted phenyl is substituted by 1, 2 or 3 substituents chosen from F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino; and
  R(13) is hydrogen, alkyl having 1, 2, 3 or 4 carbon atoms or CF$_3$;
R(2) is hydrogen, alkyl having 1, 2, 3 or 4 carbon atoms or CF$_3$;
R(3) is C$_y$H$_{2y}$—R(16);
  where y is 0, 1, 2, 3 or 4, and
  y cannot be 0 if R(16) is OR(17) or SO$_2$Me;
  R(16) is alkyl having 1, 2, 3, 4, 5 or 6 carbon atoms, cycloalkyl having 3, 4, 5, 6, 7, 8, 9, 10 or 11 carbon atoms, CF$_3$, C$_2$F$_5$, C$_3$F$_7$, CH$_2$F, CHF$_2$, OR(17), SO$_2$Me, substituted or unsubstituted phenyl, substituted or unsubstituted naphthyl, substituted or unsubstituted furyl, substituted or unsubstituted thienyl or a substituted or unsubstituted N-containing heteroaromatic having 1, 2, 3, 4, 5, 6, 7, 8 or 9 carbon atoms,
    where the substituted phenyl, substituted naphthyl, substituted furyl, substituted thienyl and the substituted N-containing heteroaromatic are each independently substituted by 1, 2 or 3 substituents chosen from F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino; and
  R(17) is hydrogen, alkyl having 1, 2, 3, 4 or 5 carbon atoms, cycloalkyl having 3, 4, 5 or 6 carbon atoms, CF$_3$, substituted phenyl, unsubstituted phenyl, substituted 2-, 3- or 4-pyridyl, or unsubstituted 2-, 3- or 4-pyridyl,
    where the substituted phenyl and substituted 2-, 3- or 4-pyridyl are each independently substituted by 1, 2 or 3 substituents chosen from F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
or
R(3) is CHR(18)R(19);
  where R(18) is hydrogen or C$_z$H$_{2z}$—R(16), where R(16) is defined as indicated above;
  z is 0, 1, 2 or 3;
  R(19) is COOH, CONH$_2$, CONR(20)R(21), COOR(22) or CH$_2$OH;
  R(20) is hydrogen, alkyl having 1, 2, 3, 4 or 5 carbon atoms, C$_v$H$_{2v}$—CF$_3$, substituted C$_w$H$_{2w}$-phenyl or unsubstituted C$_w$H$_{2w}$-phenyl,
    where the phenyl ring of the substituted C$_w$H$_{2w}$-phenyl is substituted by 1, 2 or 3 substituents chosen from F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
  v is 0, 1, 2 or 3;
  w is 0, 1, 2 or 3;
  R(21) is hydrogen or alkyl having 1, 2, 3, 4 or 5 carbon atoms; and
  R(22) is alkyl having 1, 2, 3, 4 or 5 carbon atoms;
R(4) is hydrogen, alkyl having 1, 2, 3, 4, 5 or 6 carbon atoms or CF$_3$;

or

R(3) and R(4)
together are a chain of 4 or 5 methylene groups, of which one methylene group can be replaced by —O—, —S—, —NH—, —N(methyl)- or —N(benzyl)-;

R(5) is F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino, where in the case that more than one of the radicals A1 to A8 have the meaning CR(5), the radicals R(5) are defined independently of one another;

R(30) and R(31)
independently of one another are hydrogen or alkyl having 1, 2 or 3 carbon atoms;

or

R(30) and R(31)
together are a chain of 2 methylene groups and their pharmaceutically acceptable salts.

In one embodiment, the compounds of formula 1 are those in which:

A1, A2, A3, A4, A5, A6, A7 and A8 independently of one another are chosen from nitrogen, CH or CR(5), at least 4 of these groups being CH;

R(1) is C(O)OR(9), $SO_2$R(10), COR(11) or C(O)NR(12)R(13)
where R(9), R(10), R(11) and R(12)
independently of one another are $C_xH_{2x}$—R(14);
where x is 0, 1, 2, 3 or 4; and
x cannot be 0 if R(14) is OR(15);

R(14) is alkyl having 1, 2, 3 or 4 carbon atoms, cycloalkyl having 3, 4, 5, 6, 7, 8 or 9 carbon atoms, $CF_3$, OR(15), substituted or unsubstituted phenyl, substituted or unsubstituted naphthyl, substituted or unsubstituted biphenylyl, substituted or unsubstituted furyl, substituted or unsubstituted thienyl or a substituted or unsubstituted N-containing heteroaromatic having 1, 2, 3, 4, 5, 6, 7, 8 or 9 carbon atoms, where substituted phenyl, substituted naphthyl, substituted biphenylyl, substituted furyl, substituted thienyl and the substituted N-containing heteroaromatic are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(15) is alkyl having 1, 2, 3, 4 or 5 carbon atoms, cycloalkyl having 3, 4, 5 or 6 carbon atoms, $CF_3$, substituted phenyl or unsubstituted phenyl, wherein the substituted phenyl is substituted by 1, 2 or 3 substituents chosen from F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(13) is hydrogen, alkyl having 1, 2, 3 or 4 carbon atoms or $CF_3$;

R(2) is hydrogen, alkyl having 1, 2, 3 or 4 carbon atoms or $CF_3$;

R(3) is $C_yH_{2y}$—R(16);
where y is 0, 1, 2, 3 or 4, and
y cannot be 0 if R(16) is OR(17) or $SO_2$Me;

R(16) is alkyl having 1, 2, 3, 4, 5 or 6 carbon atoms, cycloalkyl having 3, 4, 5, 6, 7, 8, 9, carbon atoms, $CF_3$, OR(17), $SO_2$Me, substituted or unsubstituted phenyl, substituted or unsubstituted naphthyl, substituted or unsubstituted furyl, substituted or unsubstituted thienyl or a substituted or unsubstituted N-containing heteroaromatic having 1, 2, 3, 4, 5, 6, 7, 8 or 9 carbon atoms, where the substituted phenyl, substituted naphthyl, substituted furyl, substituted thienyl and the substituted N-containing heteroaromatic are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(17) is hydrogen, alkyl having 1, 2, 3, 4 or 5 carbon atoms, cycloalkyl having 3, 4, 5 or 6 carbon atoms, $CF_3$, substituted phenyl, unsubstituted phenyl, substituted 2-, 3- or 4-pyridyl, or unsubstituted 2-, 3- or 4-pyridyl
where the substituted phenyl or substituted 2-, 3- or 4-pyridyl are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

or

R(3) is CHR(18)R(19);
where R(18) is hydrogen or $C_zH_{2z}$—R(16), where R(16) is defined as indicated above;
z is 0, 1, 2 or 3;

R(19) is $CONH_2$, CONR(20)R(21), COOR(22) or $CH_2$OH;

R(20) is hydrogen, alkyl having 1, 2, 3, 4 or 5 carbon atoms, $C_vH_{2v}$—$CF_3$, substituted $C_wH_{2w}$-phenyl, or substituted $C_wH_{2w}$-phenyl,
where the phenyl ring of the substituted $C_wH_{2w}$-phenyl is substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
v is 0, 1, 2 or 3;
w is 0, 1, 2 or 3;

R(21) is hydrogen or alkyl having 1, 2, 3, 4 or 5 carbon atoms; and

R(22) is alkyl having 1, 2, 3, 4 or 5 carbon atoms;

R(4) is hydrogen, alkyl having 1, 2, 3, 4, 5 or 6 carbon atoms or $CF_3$;

R(5) is F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino;

R(30) and R(31)
independently of one another are hydrogen or alkyl having 1, 2 or 3 carbon atoms;

or

R(30) and R(31)
are a chain of 2 methylene groups and their pharmaceutically acceptable salts.

In another embodiment, the compounds of formula 1 are those in which A1, A2, A3, A4, A5, A6, A7 and A8 independently of one another are chosen from nitrogen, CH or CR(5), where at most two of these groups A1–A8 are nitrogen and at least 4 of these groups are CH.

For example, in one embodiment, compounds of the formula I are those in which: A1, A2, A3, A4, A5, A6, A7 and A8 independently of one another are chosen from nitrogen, CH or CR(5), where at most two of these groups are nitrogen and at least 4 of these groups are CH;

R(1) is C(O)OR(9), SO$_2$R(10), COR(11) or C(O)NR(12)R(13);

R(9), R(10), R(11) and R(12)
independently of one another are C$_x$H$_{2x}$—R(14);
where x is 0, 1, 2, 3 or 4, and
x cannot be 0 if R(14) is OR(15);

R(14) is alkyl having 1, 2, 3, 4, 5 or 6 carbon atoms, cycloalkyl having 3, 4, 5, 6, 7, 8, 9, 10 or 11 carbon atoms, CF$_3$, C$_2$F$_5$, C$_3$F$_7$, CH$_2$F, CHF$_2$, OR(15), substituted or unsubstituted phenyl, substituted or unsubstituted naphthyl, substituted or unsubstituted biphenylyl, substituted or unsubstituted furyl, substituted or unsubstituted thienyl or a substituted or unsubstituted N-containing heteroaromatic having 1, 2, 3, 4, 5, 6, 7, 8 or 9 carbon atoms;

where the substituted phenyl, substituted naphthyl, substituted biphenylyl, substituted furyl, substituted thienyl and the substituted N-containing heteroaromatic are each independently substituted by 1, 2 or 3 substituents chosen from F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(15) is alkyl having 1, 2, 3, 4 or 5 carbon atoms, cycloalkyl having 3, 4, 5 or 6 carbon atoms, CF$_3$, substituted phenyl or unsubstituted phenyl, wherein the substituted phenyl is substituted by 1, 2 or 3 substituents chosen from F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(13) is hydrogen
R(2) is hydrogen or alkyl having 1, 2 or 3 carbon atoms;
R(3) is CHR(18)R(19);

R(18) is hydrogen or C$_z$H$_{2z}$—R(16);

R(16) is alkyl having 1, 2, 3, 4, 5 or 6 carbon atoms, cycloalkyl having 3, 4, 5, 6, 7, 8, 9, 10 or 11 carbon atoms, CF$_3$, C$_2$F$_5$, C$_3$F$_7$, CH$_2$F, CHF$_2$, OR(17), SO$_2$Me, substituted or unsubstituted phenyl, substituted or unsubstituted naphthyl, substituted or unsubstituted furyl, substituted or unsubstituted thienyl or a substituted or unsubstituted N-containing heteroatom having 1, 2, 3, 4, 5, 6, 7, 8 or 9 carbon atoms, where the substituted phenyl, substituted naphthyl, substituted furyl, substituted thienyl and the substituted N-containing heteroaromatic are each independently substituted by 1, 2 or 3 substituents chosen from F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

z is 0, 1, 2 or 3;
R(19) is CONH$_2$, CONR(20)R(21), COOR(22) or CH$_2$OH;

R(20) is hydrogen, alkyl having 1, 2, 3, 4 or 5 carbon atoms, C$_v$H$_{2v}$—CF$_3$, substituted C$_w$H$_{2w}$-phenyl, or unsubstituted C$_w$H$_{2w}$-phenyl where the phenyl ring of the substituted C$_w$H$_{2w}$-phenyl is substituted by 1, 2 or 3 substituents chosen from F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

v is 0, 1, 2 or 3;
w is 0, 1, 2 or 3;
R(21) is hydrogen or alkyl having 1, 2, 3, 4 or 5 carbon atoms;
R(22) is alkyl having 1, 2, 3, 4 or 5 carbon atoms;
R(4) is hydrogen or alkyl having 1 or 2 carbon atoms;
R(5) is F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino;

R(30) and R(31)
independently of one another are hydrogen or methyl and their pharmaceutically acceptable salts.

In a further embodiment, compounds of the formula I are those in which:

A1, A2, A3, A4, A5, A6, A7 and A8
independently of one another are chosen from nitrogen, CH or CR(5), where at most one of these groups is nitrogen and at least 5 of these groups are CH;

R(1) is C(O)OR(9), SO$_2$R(10), COR(11) or C(O)NR(12)R(13);

where R(9), R(10), R(11) and R(12)
independently of one another are C$_x$H$_{2x}$—R(14);
x is 0, 1, 2, 3 or 4;

R(14)
is alkyl having 1, 2, 3 or 4 carbon atoms, cycloalkyl having 3, 4, 5, 6, 7, 8 or 9 carbon atoms, CF$_3$, substituted or unsubstituted phenyl, substituted or unsubstituted naphthyl, substituted or unsubstituted biphenylyl, substituted or unsubstituted furyl, substituted or unsubstituted thienyl or a substituted or unsubstituted N-containing heteroaromatic having 1, 2, 3, 4, 5, 6, 7, 8 or 9 carbon atoms, where the substituted phenyl, substituted naphthyl, substituted biphenylyl, substituted furyl, substituted thienyl and the substituted N-containing heteroaromatic are each independently substituted by 1, 2 or 3 substituents chosen from F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(13) is hydrogen;
R(2) is hydrogen or methyl;
R(3) is C$_y$H$_{2y}$—R(16);
where y is 0, 1, 2, 3 or 4; and
y cannot be 0 if R(16) is OR(17);

R(16) is alkyl having 1, 2, 3, 4, 5 or 6 carbon atoms, cycloalkyl having 3, 4, 5, 6, 7, 8 or 9 carbon atoms, CF$_3$, OR(17), SO$_2$Me, substituted or unsubstituted phenyl, substituted or unsubstituted naphthyl, substituted or unsubstituted furyl, substituted or unsubstituted thienyl or a substituted or unsubstituted N-containing heteroaromatic having 1, 2, 3, 4, 5, 6, 7, 8 or 9 carbon atoms, where the substituted phenyl, substituted naphthyl, substituted furyl, substituted thienyl and the substituted N-containing heteroaromatic are each independently substituted by 1, 2 or 3 substituents chosen from F, Cl, Br, I, $CF_3$, $NO_2$, $OCF_3$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(17) is hydrogen, alkyl having 1, 2, 3, 4 or 5 carbon atoms, cycloalkyl having 3, 4, 5 or 6 carbon atoms, $CF_3$, substituted phenyl, unsubstituted phenyl, substituted 2-, 3- or 4-pyridyl, or unsubstituted 2-, 3- or 4-pyridyl where the substituted phenyl or substituted 2-, 3- or 4-pyridyl are each independently substituted by 1, 2 or 3 substituents chosen from F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(4) is hydrogen or alkyl having 1 or 2 carbon atoms;

R(5) is F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino;

R(30) and R(31)
independently of one another are hydrogen or methyl;
and their pharmaceutically acceptable salts.

In another embodiment, the compounds of the formula I are those in which
A4 is CH or nitrogen;
A1, A2, A3, A5, A6, A7 and A8
independently of one another are chosen from CH or CR(5),
where at least 5 of these groups are CH.

In an even further embodiment, the compounds of the formula I are those in which:
R(1) is C(O)OR(9), $SO_2R(10)$, COR(11) or C(O)NR(12)R(13);
where R(9), R(10), R(11) and R(12)
independently of one another are $C_xH_{2x}$—R(14);
where x is 0, 1, 2 or 3;
R(14) is alkyl having 1, 2, 3 or 4 carbon atoms, cycloalkyl having 3, 4, 5, 6, 7, 8 or 9 carbon atoms, $CF_3$, substituted phenyl, unsubstituted phenyl, substituted pyridyl, or unsubstituted pyridyl where the substituted phenyl and substituted pyridyl are each independently substituted by 1 or 2 substituents chosen from F, Cl, Br, I, $CF_3$, $OCF_3$, OH, alkyl having 1, 2 or 3 carbon atoms or alkoxy having 1 or 2 carbon atoms;

R(13) is hydrogen;
R(2) is hydrogen;
R(3) is $C_yH_{2y}$—R(16),
y is 0, 1 or 2;
R(16) is alkyl having 1, 2, 3 carbon atoms, cycloalkyl having 5 or 6 carbon atoms, $CF_3$, substituted phenyl, unsubstituted phenyl, substituted pyridyl, or unsubstituted pyridyl where the substituted phenyl and substituted pyridyl are each independently substituted by 1 or 2 substituents chosen from F, Cl, $CF_3$, alkyl having 1, 2 or 3 carbon atoms and alkoxy having 1 or 2 carbon atoms;

R(4) is hydrogen;
R(5) is F, Cl, $CF_3$, CN, COOMe, $CONH_2$, COMe, $NH_2$, OH, alkyl having 1, 2 or 3 carbon atoms or alkoxy having 1 or 2 carbon atoms;

R(30) and R(31)
independently of one another are hydrogen or methyl;
and their pharmaceutically acceptable salts.

Another example of the compounds of the formula I are those in which:
R(1) is C(O)OR(9) or COR(11);
where R(9) and R(11)
independently of one another are $C_xH_{2x}$—R(14);
where x is 0, 1, 2 or 3;
R(14) is cycloalkyl having 5 or 6 carbon atoms, substituted phenyl, or unsubstituted phenyl
where the substituted phenyl is substituted by 1 or 2 substituents chosen from F, Cl, Br, I, $CF_3$, $OCF_3$, OH, alkyl having 1, 2 or 3 carbon atoms or alkoxy having 1 or 2 carbon atoms;

R(2) is hydrogen;
R(3) is $C_yH_{2y}$—R(16);
y is 0, 1 or 2;
R(16) is alkyl having 1, 2 or 3 carbon atoms, cycloalkyl having 5 or 6 carbon atoms, substituted phenyl, unsubstituted phenyl, substituted pyridyl, or unsubstituted pyridyl,
where the substituted phenyl and substituted pyridyl are each independently substituted by 1 or 2 substituents chosen from F, Cl, $CF_3$, $OCF_3$, alkyl having 1, 2 or 3 carbon atoms and alkoxy having 1 or 2 carbon atoms;

R(4) is hydrogen;
R(5) is F, Cl, alkyl having 1, 2 or 3 carbon atoms or alkoxy having 1 or 2 carbon atoms;

R(30) and R(31)
are hydrogen;
and their pharmaceutically acceptable salts.

The invention also relates to the preparation of the compounds of the invention and to their use, in particular in pharmaceuticals.

The compounds according to the invention were hitherto, to the best of our knowledge, unknown. Not to be limited as to theory, they act on the 'Kv1.5 potassium channel' and, as an ultra-rapidly activating delayed rectifier, inhibit a designated potassium current in the human atrium. The compounds may therefore be suitable as novel antiarrhythmic active compounds, in particular for the treatment and prophylaxis of atrial arrhythmias, e.g. (atrial fibrillation AF) or atrial flutters.

Atrial fibrillation (AF) and atrial flutters are the most frequent persistent cardiac arrhythmias. Occurrence increases with increasing age and frequently leads to fatal sequelae, such as cerebral stroke. AF affects about 1 million Americans annually and leads to more than 80,000 cases of stroke each year in the USA. The presently customary antiarrhythmics of classes I and III reduce the reoccurrence rate of AF, but are only of restricted use because of their potential proarrhythmic side effects. There is therefore a great medical need for the development of better medicaments for treating atrial arrhythmias (S. Nattel, Am. Heart J. 130, 1995, 1094–1106; "Newer developments in the management of atrial fibrillation").

It has been shown that most supraventricular arrhythmias are subject to "reentry" excitatory waves. Such reentries occur when the cardiac tissue has a slow conductivity and, at the same time, very short refractory periods. Increasing the myocardial refractory period by prolonging the action potential is a recognized mechanism of ending arrhythmias or preventing their formation (T. J. Colatsky et al, Drug Dev. Res. 19, 1990, 129–140; "Potassium channels as targets for antiarrhythmic drug action"). The length of the action potential is essentially determined by the extent of repolarizing K+ currents which flow out of the cell from various K+ channels. Particularly high importance is ascribed here to the 'delayed rectifier' $I_K$, which consists of 3 different components, $IK_r$, $IK_s$ and $IK_{ur}$.

Most known class III antiarrhythmics (e.g. dofetilide, E4031 and d-sotalol) mainly or exclusively block the rapidly activating potassium channel $IK_r$, which can be demonstrated both in cells of the human ventricle and in the atrium. However, it has been shown that these compounds have an increased proarrhythmic risk at low or normal heart rates, arrhythmias which are designated as "torsades de pointes" being observed (D. M. Roden, Am. J. Cardiol. 72, 1993, 44B–49B; "Current status of class III antiarrhythmic drug therapy"). In addition to this high, in some cases fatal risk at a low rate, a decrease in the activity has been found for the $I_{Kr}$ blockers under the conditions of tachycardia, in which the action is especially needed ("negative use-dependence").

While some of these disadvantages can possibly be overcome by blockers of the slow-activating component ($IK_s$), their activity has hitherto been unconfirmed, since no clinical investigations using $IK_s$ channel blockers are known.

The "particularly rapidly" activating and very slowly inactivating component of the delayed rectifier $IK_{ur}$ (=ultra-rapidly activating delayed rectifier), which corresponds to the Kv1.5 channel, plays a particularly large role in the repolarization period in the human atrium. Inhibition of the $IK_{ur}$ potassium outward current is thus, in comparison with the inhibition of $IK_r$ or $IK_s$, a particularly effective method for prolonging the atrial action potential and thus for the ending or prevention of atrial arrhythmias. Mathematical models of the human action potential suggest that the positive effect of a blockade of the $IK_{ur}$, especially under the pathological conditions of chronic atrial fibrillation, should be particularly pronounced (M. Courtemanche, R. J. Ramirez, S. Nattel, Cardiovascular Research 1999, 42, 477–489: "Ionic targets for drug therapy and atrial fibrillation-induced electrical remodeling: insights from a mathematical model").

In contrast to $IK_r$ and $IK_s$, which also occur in the human ventricle, the $IK_{ur}$ indeed plays an important role in the human atrium, but not in the ventricle. For this reason, in the case of inhibition of the $IK_{ur}$ flow, in contrast to the blockade of $IK_r$ or $IK_s$, the risk of a proarrhythmic action on the ventricle is excluded from the start (Z. Wang et al, Circ. Res. 73, 1993, 1061–1076).

Antiarrhythmics which act via selective blockade of the $IK_{ur}$ current or Kv1.5 channel have hitherto not been available, however, on the market. For numerous pharmaceutical active compounds (e.g. tedisamil, bupivacaine or sertindole), a blocking action on the Kv1.5 channel has indeed been described, but the Kv1.5 blockade here is in each case only a side effect in addition to other main actions of the substances.

WO 98 04 521 and WO 99 37 607 claim aminoindans and aminotetrahydro-naphthalenes as potassium channel blockers which block the Kv1.5 channel. Likewise, structurally related aminochromans are claimed as Kv1.5 blockers in WO 00 12 077. The application WO 99 62 891 claims thiazolidinones which likewise block the potassium channel. The applications WO 98 18475 and WO 98 18476 claim the use of various pyridazinones and phosphine oxides as antiarrhythmics which should act via blockade of the $Ik_{ur}$. The same compounds were originally also described, however, as immunosuppressants (WO 96 25 936). All compounds described in the abovementioned applications are structurally completely different to the compounds according to the invention of this application. For all compounds claimed in the abovementioned applications, no clinical data are known to use.

It has now surprisingly been found that the ortho, meta-substituted bisaryl compounds described here are potent blockers of the human Kv1.5 channel. They may therefore, for example, be used as novel antiarrhythmics having a particularly advantageous safety profile. For example, the compounds may be suitable for the treatment of supraventricular arrhythmias, e.g. atrial fibrillation or atrial flutters.

In one embodiment of the invention, the compounds may be employed for the termination of existing atrial fibrillation or flutters for the recovery of the sinus rhythm (cardio version). Moreover, the substances reduce the susceptibility to the formation of new fibrillation events (maintenance of the sinus rhythm, prophylaxis).

The compounds according to the invention were hitherto, to the best of our knowledge, unknown.

Some structurally related compounds which are not part of this invention are described in Symett, 1994, 349 and Can. J. Chem. 2000, 905. The compound A mentioned there

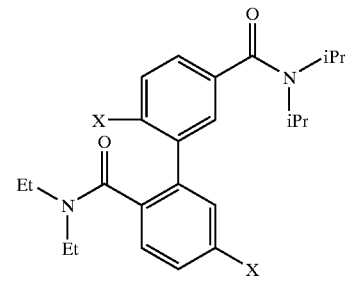

X = H or Methyl have a carboxamide group in the ortho position to the second phenyl ring, and a potassium channel-blocking activity is not described.

According to the invention, alkyl radicals and alkylene radicals can be straight-chain or branched. This also applies to the alkylene radicals of the formulae $C_xH_{2x}$, $C_yH_{2y}$, $C_zH_{2z}$, $C_vH_{2v}$ and $C_wH_{2w}$. Alkyl radicals and alkylene radicals can also be straight-chain or branched if they are substituted or are contained in other radicals, e.g. in an alkoxy radical or in a fluorinated alkyl radical. Non-limiting examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, eicosyl. The divalent radicals derived from these radicals, e.g., methylene, 1,1-ethylene, 1,2-ethylene, 1,1-propylene, 1,2-propylene, 2,2-propylene, 1,3-propylene, 1,1-butylene, 1,4-butylene, 1,5-pentylene, 2,2-dimethyl-1,3-propylene, 1,6-hexylene, etc. are non-limiting examples of alkylene radicals.

Cycloalkyl radicals can likewise be branched. Non-limiting examples of cycloalkyl radicals having 3 to 11 carbon atoms are cyclopropyl, cyclobutyl, 1-methylcyclopropyl, 2-methylcyclopropyl, cyclopentyl, 2-methylcyclobutyl, 3-methylcyclobutyl, cyclopentyl, cyclohexyl, 2-methylcyclohexyl, 3-methylcyclohexyl, 4-methylcyclohexyl, menthyl, cycloheptyl, cyclooctyl etc.

N-containing heteroaromatics having 1, 2, 3, 4, 5, 6, 7, 8 or 9 carbon atoms include, but are note limited to, 1-, 2- or 3-pyrrolyl, 1-, 2-, 4- or 5-imidazolyl, 1-, 3-, 4- or 5-pyrazolyl, 1,2,3-triazol-1-, -4- or 5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazol 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also included are the corresponding N-oxides of these compounds, i.e., for example, 1-oxy-2-, -3- or -4-pyridyl.

In one embodiment, N-containing heterocycles are pyrrolyl, imidazolyl, quinolyl, pyrazolyl, pyridyl, pyrazinyl, pyrimidinyl and pyridazinyl.

Pyridyl is either 2-, 3- or 4-pyridyl. Thienyl is either 2- or 3-thienyl. Furyl is either 2- or 3-furyl.

Monosubstituted phenyl radicals can be substituted in the 2-, the 3- or the 4-position, disubstituted in the 2,3-, 2,4-, 2,5-, 2,6-, 3,4- or 3,5-position, or trisubstituted in the 2,3,4-, 2,3,5-, 2,3,6-, 2,4,5-, 2,4,6- or 3,4,5-position. Correspondingly, the same analogously also applies to the N-containing heteroaromatics, the thiophene or the furyl radical.

In the case of di- or trisubstitution of a radical, the substituents can be identical or different.

In one embodiment, if R(3) and R(4) together are a chain of 4 or 5 methylene groups, of which one methylene group can be replaced by —O—, —S—, —NH— etc., then these radicals together with the nitrogen atom may form a 5- or 6-membered nitrogen heterocycle, such as pyrrolidine, piperidine, morpholine, thiomorpholine etc.

In a further embodiment, if the compounds of the invention contain one or more acidic or basic groups or one or more basic heterocycles, the invention also includes the corresponding physiologically or toxicologically tolerable salts, in particular the pharmaceutically utilizable salts. Thus the compounds of the formula I which carry acidic groups, e.g. one or more COOH groups, can be used, for example, as alkali metal salts, preferably sodium or potassium salts, or as alkaline earth metal salts, e.g. calcium or magnesium salts, or as ammonium salts, e.g. as salts with ammonia or organic amines or amino acids. Compounds of the invention which carry one or more basic, i.e. protonatable, groups or contain one or more basic heterocyclic rings can also be used in the form of their physiologically tolerable acid addition salts with inorganic or organic acids, for example as hydrochlorides, phosphates, sulfates, methanesulfonates, acetates, lactates, maleates, fumarates, malates, gluconates, etc. If the compounds of the invention simultaneously contain acidic and basic groups in the molecule, in addition to the salt forms described, the invention also includes internal salts, 'betaines'. Salts may be obtained from the compounds of the invention according to customary processes, for example, by combination with an acid or base in a solvent or dispersant or alternatively from other salts by anion exchange.

In one embodiment, if appropriately substituted, the compounds of the formula I can be present in stereoisomeric forms. If the compounds of the formula I contain one or more centers of asymmetry, these can independently of one another have the S configuration or the R configuration. The invention includes all possible stereoisomers, e.g. enantiomers or diastereomers, and mixtures of two or more stereoisomeric forms, e.g. enantiomers and/or diastereomers, in any desired ratios. The invention thus includes enantiomers, e.g. in enantiomeric pure form, both as levo- and dextrorotatary antipodes, and in the form of mixtures of the two enantiomers in different ratios or in the form of racemates. Individual stereoisomers can be prepared, if desired, by separation of a mixture according to customary methods or, for example, by stereoselective synthesis. If mobile hydrogen atoms are present, the present invention also includes all tautomeric forms of the compounds of the formula I.

The compounds of the invention may be prepared by different chemical processes, which are likewise encompassed by the present invention. Some typical routes are outlined in the reaction sequences designated below as Schemes 1 to 4. A1 to A8 and the radicals R(1) to R(4), R(30) and R(31) are in each case defined as indicated above, if not stated otherwise below.

Thus a compound of the formula I, for example, is obtained as in Scheme 1 (method A) or Scheme 2 (method B).

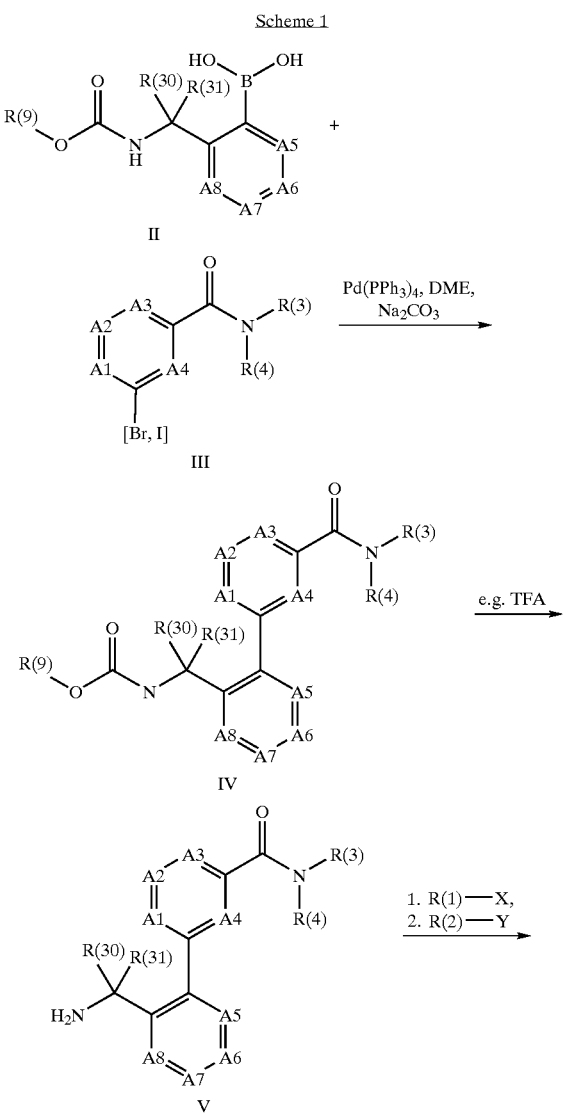

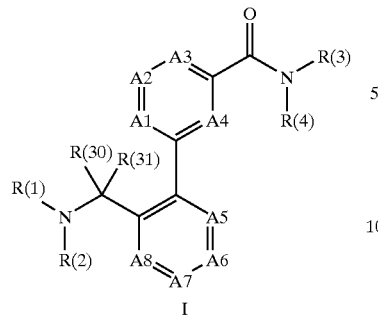

I

Bisaryls of the formula IV may be prepared by palladium-catalyzed Suzuki coupling (which can be carried out, for example, in the presence of $Pd[(PPh_3)]_4$ as a catalyst, sodium carbonate as a base and 1,2-dimethoxyethane as a solvent) of an aromatic halide of the formula III with an aromatic boronic acid of the formula II. If R(9) is an easily cleavable radical, such as tert-butyl or benzyl, compounds of the formula V can be obtained, which can then be converted into compounds of the formula I by reaction with reagents R(1)-X and/or R(2)-Y. The reactions of the compounds of the formula V with compounds of the formula R(1)-X correspond to the known conversion of an amine into a carboxamide, sulfonamide, carbamate, urea or thiourea derivative. The radical X here is a suitable nucleofugic leaving group, such as F, Cl, Br, imidazole, O-succinimide etc.

For the preparation of the compounds of the formula I in which R(1) is C(O)OR(9), i.e. carbamates, compounds of the formula R(1)-X, for example, are used in which X may be chlorine or O-succinimide, i.e. chloroformates or succinimidocarbonates.

For the preparation of compounds of the formula I in which R(1) is $SO_2R(10)$, i.e. sulfonamides, compounds of the formula R(1)-X may be used in which X is chlorine, i.e. sulfonyl chlorides.

For the preparation of compounds of the formula I in which R(1) is COR(11), i.e. carboxamides, compounds of the formula R(1)-X, for example, may be used in which X is chlorine, imidazole or acetoxy, i.e. carboxylic acid chlorides, carboxylic acid imidazolides or mixed anhydrides. However, it is also possible, for example, to use the free acids of the formula R(1)—OH in the presence of suitable condensing agents such as carbodiimides or TFFH.

For the preparation of compounds of the formula I in which R(1) is CONR(12)R(13) or C(S)NR(12)R(13), i.e. ureas or thioureas, instead of the compounds of the formula R(1)—X compounds of the formula R(12)N(=C=O) or R(12)N(=C=S) may also be used, i.e. isocyanates or isothiocyanates.

Scheme 2

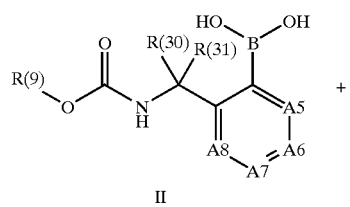

II

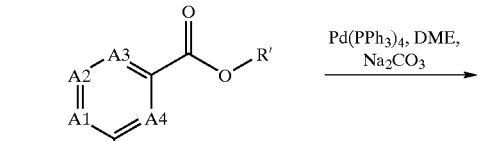

VII

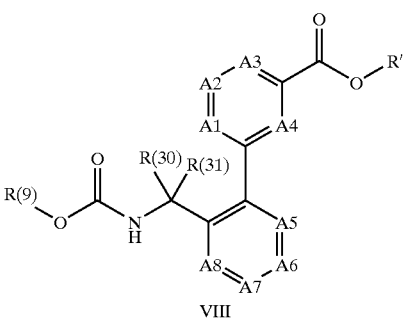

VIII

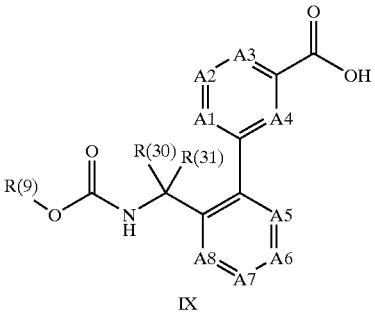

IX

IV $\xrightarrow{\text{e.g. TFA}}$ V $\xrightarrow[\text{2. R(2)—Y}]{\text{1. R(1)—X,}}$ I Bisaryls of the formula VIII may be prepared by palladium-catalyzed Suzuki coupling of an aromatic bromide, iodide or chloride of the formula VII with an aromatic boronic acid of the formula II (Scheme 2). Hydrolysis of the ester using, for example, LiOH affords the free acids of the formula IX which can be converted into the bisaryls of the formula IV by coupling with amines NHR(3)R(4). As described in Scheme 1, cleavage of the labile group R(9) yields compounds of the formula V, which can be further converted to compounds of the formula I.

The abovementioned reactions of the compounds of the formula IX with amines of the formula HNR(3)R(4) correspond to the known conversion of a carboxylic acid to a carboxamide. Numerous methods for carrying out these reactions have been described in the literature. They may be carried out, for example, by activation of the carboxylic acid, e.g. using dicyclohexylcarbodiimide (DCC) or N-(3-dimethylaminopropyl)-N'-ethylcarbodiimide hydrochloride (EDC), if appropriate with addition of hydroxybenzotriazole (HOBt) or dimethylaminopyridine (DMAP). However, reactive acid derivatives can also first be synthesized by known methods, e.g. acid chlorides by reaction of the carboxylic acids of the formula IX or using inorganic acid halides, e.g. $SOCl_2$, or acid imidazolides by reaction with carbonyldiimidazole, which are then subsequently reacted with the amines of the formula HNR(3)R(4), if appropriate with addition of an auxiliary base.

Scheme 3

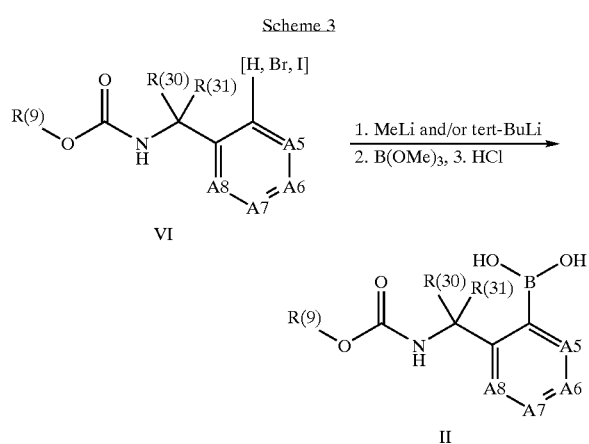

The aromatic boronic acids of the formula II needed in methods A and B may be synthesized from the aromatics or aromatic halides of the formula VI by ortholithiation or halogen-metal exchange followed by reaction with trimethyl borates (or other boric acid triesters) and subsequent acidic hydrolysis.

Scheme 4

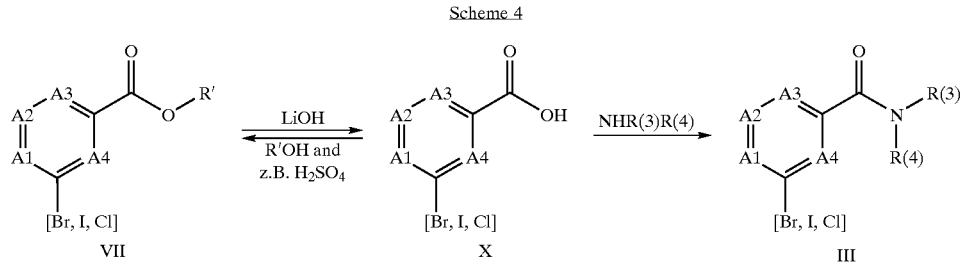

The halides of the formula VII employed in method B may be synthesized by procedures known from the literature or are readily obtainable from the acids of the formula X known from the literature by customary esterification methods. The aromatic ortho-haloamides of the formula III employed in method A are obtainable, for example, according to scheme 4 from the esters of the formula VII, after hydrolysis to the acids X, by coupling with amines NHR(3)R(4). The linkage of the amide bond can be carried out in the ways described above for the reaction of compounds of the formula IX to IV.

In all procedures, it may be appropriate to temporarily protect functional groups in the molecule in certain reaction steps. Such protective group techniques are familiar to the person skilled in the art. The choice of a protective group for possible groups and the processes for its introduction and removal are described in the literature and can be adapted to the individual case, if appropriate, without difficulties.

In one embodiment, the compounds of the formula I according to the invention and their physiologically tolerable salts may be used in animals, preferably in mammals, and in particular in humans, as pharmaceuticals per se, in mixtures with one another or in the form of pharmaceutical preparations. The present invention, in one embodiment, also relates to the compounds of the formula I and their physiologically tolerable salts for use as pharmaceuticals, their use in the therapy and prophylaxis of the syndromes mentioned and their use for the production of medicaments therefor and of medicaments having $K^+$ channel-blocking action. The present invention furthermore, in a further embodiment, relates to pharmaceutical preparations which, as active constituent, contain an efficacious dose of at least one compound of the formula I and/or of a physiologically tolerable salt thereof in addition to customary, pharmaceutically innocuous vehicles and excipients. The pharmaceutical preparations, for example, contain 0.1 to 90 percent by weight of the compounds of the formula I and/or their physiologically tolerable salts. The pharmaceutical preparations may, for example, be prepared in a manner known per se. To this end, the compounds of the formula I and/or their physiologically tolerable salts may be brought, together with one or more solid or liquid pharmaceutical vehicles and/or excipients and, if desired, in combination with other pharmaceutically active compounds, into a suitable administration or dose form, which can then be used as a pharmaceutical in human medicine or veterinary medicine.

Pharmaceuticals which contain compounds of the formula I according to the invention and/or their physiologically tolerable salts may be administered, for example, orally, parenterally, e.g. intravenously, rectally, by inhalation or topically, the preferred administration being dependent on the individual case, e.g. the particular clinical picture of the condition to be treated.

The person skilled in the art is familiar on the basis of his/her expert knowledge with excipients which are suitable for the desired pharmaceutical formulation. In addition to solvents, gel formers, suppository bases, tablet excipients and other active compound carriers, it is possible to use, for example, antioxidants, dispersants, emulsifiers, antifoams, flavor corrigents, preservatives, solubilizers, agents for achieving a depot effect, buffer substances or colorants.

In one embodiment, the compounds of the formula I may also be combined with other pharmaceutical active compounds to achieve an advantageous therapeutic action. Thus, for example, in the treatment of cardiovascular conditions advantageous combinations with cardiovascular-active substances are possible. Suitable combination partners of this type which may be advantageous for cardiovascular conditions are, for example, other antiarrhythmics, i.e. class I, class II or class III antiarrhythmics, such as $IK_s$ or $IK_r$ channel blockers, e.g. dofetilide, or furthermore blood pressure-lowering substances such as ACE inhibitors (for example enalapril, captopril, ramipril), angiotensin antagonists, $K^+$ channel activators, and also alpha- and beta-receptor blockers, but also sympathomimetic compounds and compounds having adrenergic activity, and also $Na^+/H^+$ exchange inhibitors, calcium channel antagonists, phosphodiesterase inhibitors and other substances having positive inotropic action, such as digitalis glycosides, or diuretics.

In one embodiment, for a form for oral administration, the active compounds are mixed with the additives suitable therefor, such as vehicles, stabilizers or inert diluents, and brought by means of the customary methods into the suitable administration forms, such as tablets, coated tablets, hard gelatin capsules, aqueous, alcoholic or oily solutions. Inert carriers which can be used are, for example, gum arabic, magnesia, magnesium carbonate, potassium phosphate, lactose, glucose or starch, in particular cornstarch. In this case, preparation can be carried out, for example, either as dry or as moist granules. Possible oily vehicles or solvents are, for example, vegetable or animal oils, such as sunflower oil or cod liver oil. Possible solvents for aqueous or alcoholic solutions are, for example, water, ethanol or sugar solutions or mixtures thereof. Further excipients, also for other administration forms, are, for example, polyethylene glycols and polypropylene glycols.

For subcutaneous or intravenous administration, the active compounds, if desired with the substances customary therefor, such as solubilizers, emulsifiers or further excipients, may be brought into solution, suspension or emulsion. The compounds of the formula I and their physiologically tolerable salts can also be lyophilized and the lyophilizates obtained used, for example, for the production of injection or infusion preparations. Possible solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the active compounds of the formula I or their physiologically tolerable salts in a pharmaceutically acceptable solvent, such as, in particular, ethanol or water, or a mixture of such solvents. If required, the formulation can also additionally contain other pharmaceutical excipients such as surfactants, emulsifiers and stabilizers, and also a propellant. Such a preparation may contain the active compound, for example, in a concentration of approximately 0.1 to 10, in particular of approximately 0.3 to 3, percent by weight.

The dose of the active compound of the formula I to be administered or of the physiologically tolerable salts thereof depends on the individual case and is to be adapted to the conditions of the individual case as customary for an optimal action. Thus it depends, of course, on the frequency of administration and on the potency and duration of action of the compounds in each case employed for therapy or prophylaxis, but also on the nature and severity of the disease to be treated, and on the sex, age, weight and individual responsiveness of the human or animal to be treated and on whether therapy is carried out acutely or prophylactically. Customarily, the daily dose of a compound of the formula I when administered to a patient weighing approximately 75 kg is 0.001 mg/kg of body weight to 100 mg/kg of body weight, preferably 0.01 mg/kg of body weight to 20 mg/kg of body weight. The dose can be administered in the form of an individual dose or in a number of doses, e.g. 2, 3 or 4 individual doses. In particular when treating acute cases of cardiac arrhythmias, for example in an intensive care unit, parenteral administration by injection or infusion, e.g. by means of an intravenous continuous infusion, can also be advantageous.

EXPERIMENTAL SECTION

List of Abbreviations
Boc tert-butyloxycarbonyl
DCC dicyclohexylcarbodiimide
DIPEA N-ethyldiisopropylamine
DMAP 4-dimethylaminopyridine
DME 1,2-dimethoxyethane
EDC N-(3-dimethylaminopropyl)-N'-ethylcarbodiimide hydrochloride
Eq. molar equivalent
HOBt 1-hydroxy-1H-benzotriazole
Me methyl
MeLi methyllithium (in hexane)
BuLi butyllithium (in pentane)
RT room temperature
RP-HPLC reverse-phase high-performance chromatography
THF tetrahydrofuran
TFFH tetramethylfluoroamidinium hexafluorophosphate
TFA trifluoroacetic acid Synthesis of the Boronic Acids of the Formula II The boronic acids were synthesized as in scheme 3—their synthesis is demonstrated with the aid of a plurality of compounds:

2-(tert-Butoxycarbonylaminomethyl)phenylboronic acid (Compound 1)

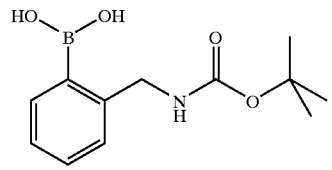

N-Boc-2-bromobenzylamine (5.72 g, 20 mmol) was dissolved in THF under argon, the solution was cooled to −78° C., treated with 13.75 ml of MeLi (1.6 M in hexane, 22 mmol) and, after 1 h, with 28 ml (1.5 M in pentane, 42 mmol) of tert-BuLi and, after a further hour, trimethyl borate (9.0 ml, 80 mmol) was added at −78° C. After warming to room temperature, the mixture was treated with dilute hydrochloric acid to pH 6, extracted with dichloromethane, and the organic phase was washed with saturated NaCl solution and dried. 5.1 g (100%) of a pale yellow solid foam were obtained.

MS (FAB, sample treated with glycerol): m/z=308 (M+57), 252 (M+1).

(R)-2-(1-tert-Butoxycarbonylaminoethyl)phenylboronic acid (Compound 2)

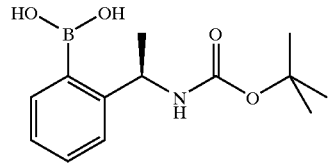

2.2 g (10 mmol) of N-Boc-(R)-phenethylamine were dissolved in 50 ml of anhydrous THF, and the solution was cooled to −78° C. and treated dropwise with 14 ml (1.5 M solution in pentane, 21 mmol) of tert-butyllithium. The mixture was warmed to −20° C. in the course of 2 h, then 4.5 ml (40 mmol) of trimethyl borate were added and the mixture was warmed to room temperature. The solution was cooled to 0° C., acidified to pH 6 with 10% HCl, the aqueous phase was extracted with dichloromethane, and the combined organic phases were washed with saturated NaCl solution, dried and concentrated. 2.0 g (75%) of a pale yellow solid foam were obtained which was used without further purification. MS (FAB, sample treated with glycerol): m/z=322 (M+57), 266 (M+1).

3-(tert-Butoxycarbonylaminomethyl)pyridine-4-boronic acid (Compound 3)

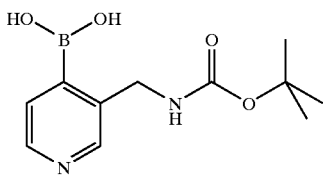

5.5 g (26.4 mmol) of N-Boc-3-aminomethylpyridine were dissolved in THF, cooled to −78° C., treated with 37 ml of tert-BuLi (1.5 M in pentane, 55.5 mmol) and the deep-green mixture was slowly warmed to −20° C. After addition of trimethyl borate (12 ml, 105.6 mmol), the mixture was warmed to room temperature and stirred overnight. After addition of dilute hydrochloric acid to pH 6, the solution was concentrated on a rotary evaporator and extracted with chloroform/isopropanol (3/1). The organic phase was dried and concentrated. 4.3 g (65%) of an orange solid were obtained which was employed without further purification. MS (FAB, sample treated with glycerol): m/z=309 (M+57).

Synthesis of Aromatic Halides of the Formulae III and VII

General Working Procedure for the Synthesis of the Compounds of the Formula VII Using Thionyl Chloride:

2.5 mmol of acid of the formula X are heated to reflux for 4 h with 3 ml of thionyl chloride and then concentrated. The crude reaction product is coevaporated twice with toluene, taken up in 12.5 ml of dichloromethane and treated with 3 mmol of the amine NHR(3)R(4) and 5.5 mmol of triethylamine. The mixture is stirred overnight, washed with NaHCO$_3$ solution, dried and concentrated. 1.5 to 2.5 mmol of the desired amide III are obtained, which can be employed without further purification.

Examples of Amides III According to the General Working Procedure

| Compound | Structure | Mass (ES+): m/z = |
|---|---|---|
| 4 | | 270 (M + 1) |
| 5 | | 326 (M + 1) |
| 6 | | 360 (M + 1) |
| 7 | 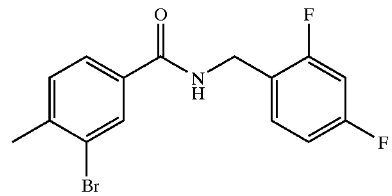 | 340 (M + 1) |
| 8 | 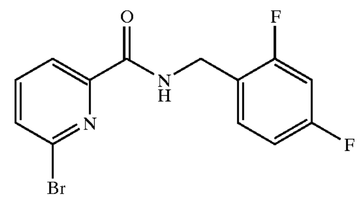 | 327 (M + 1) |
| 9 | 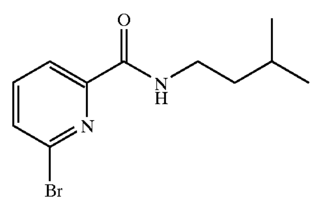 | 271 (M + 1) |
| 10 | 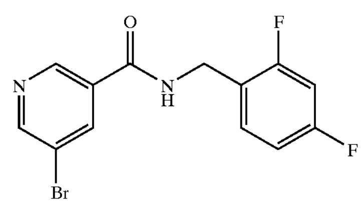 | 327 (M + 1) |
| 11 | 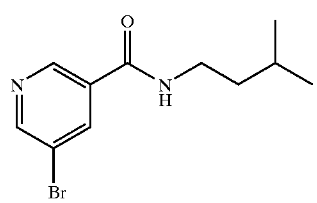 | 271 (M + 1) |

The esters VII were synthesized according to procedures known from the literature, in some cases from the acids X by esterification according to processes customary in the laboratory.

Example of Ester Halide VII

| Compound | Structure | Mass |
|---|---|---|
| 12 | 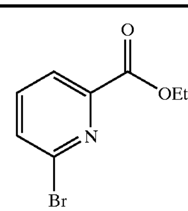 | acid commercially obtainable |

Synthesis of the Bisaryls by Palladium-catalyzed Suzuki Coupling to the Compounds of the Formulae IV (Scheme 1) and VIII (Scheme 2)

General Working Procedure:

0.05 eq. of tetrakistriphenylphosphinepalladium and 1 eq. of the corresponding bromide III or VII were added to 1,2-dimethoxyethane (10 ml/mmol of bromide III or VII) aerated with argon. After 10 min, 1.5 eq. of the corresponding boronic acid were added and finally 2 eq. of a 2 molar sodium carbonate solution. The mixture was heated to reflux under argon for 18 h, cooled and diluted with methylene chloride. The mixture was washed with water and saturated sodium chloride solution, dried over sodium sulfate, concentrated and purified by chromatography. In the RP-HPLC purification, basic compounds were isolated as trifluoroacetates.

Examples of Bisaryls of the Formula VIII

Ethyl 6-[2-(tert-butoxycarbonylaminomethyl)phenyl]pyridine-2-carboxylate (compound 13)

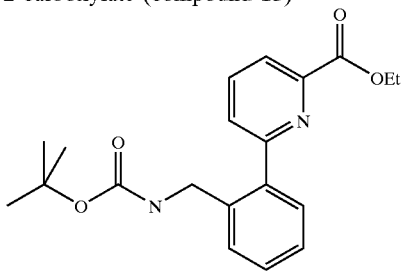

83 ml of 1,2-dimethoxyethane were aerated with argon, and 481 mg (0.41 mmol) of Pd(PPh$_3$)$_4$ and 1.9 g (8.3 mmol) of ethyl 6-bromopicolinate were added. After 10 min, 3.16 g (12.5 mmol) of 2-(tert-butoxycarbonylaminomethyl)phenylboronic acid and finally 8.3 ml of a 2M sodium carbonate solution were added. The mixture was heated to reflux under argon for 18 h, diluted with dichloromethane after cooling and washed with water. The organic phase was dried, concentrated and purified by chromatography on silica gel. 2.12 g (72%) of a viscous orange oil were obtained.

MS (ES+): m/z=357 (M+1).

$^1$H-NMR (CDCl$_3$): δ=8.13 (1H, dd, J=7.7, 1.1 Hz); 7.96 (1H, t, J=7.7 Hz); 7.7 (1H, dd, J=7.7, 1.1 Hz); 7.74 (1H, d, J=7.7 Hz); 7.52–7.38 (3H, m); 7.04 (1H, m); 4.54 (2H, q, J=7.0 Hz); 4.22 (2H, m); 1.46 (9H, s); 1.44 (3H, t, J=7.0 Hz).

Examples of Bisaryls of the Formula IV (according to method A)

The following compounds, which are simultaneously examples, were synthesized according to the abovementioned general working procedure:

| Example | Structure | Mass (ES+): m/z = |
|---|---|---|
| 1 | 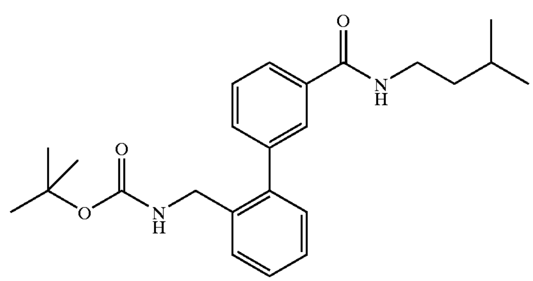 | 382 (M + 1) |
| 2 | 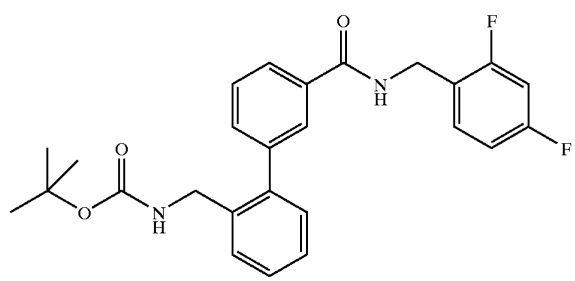 | 453 (M + 1) |
| 3 | 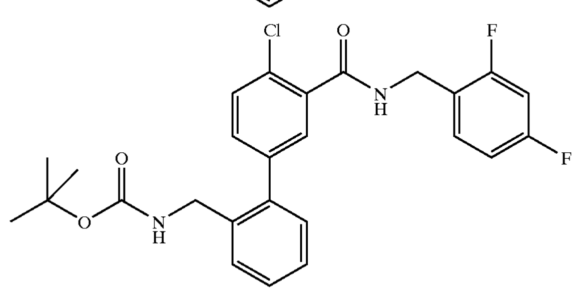 | 487 (M + 1), 431 (M − 55) |

| Example | Structure | Mass (ES+): m/z = |
|---------|-----------|-------------------|
| 4 | 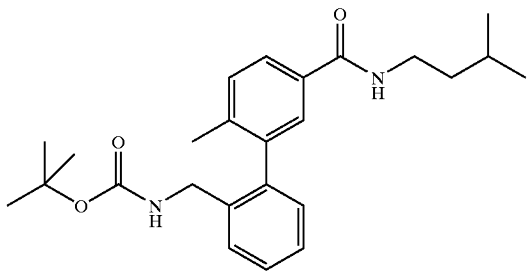 | 411 (M + 1) |
| 5 | 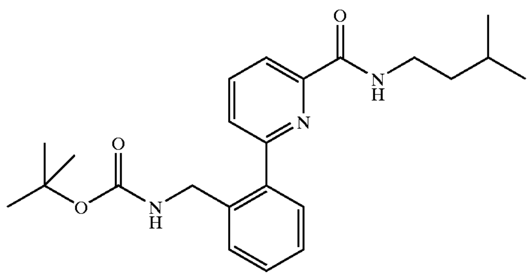 | 398 (M + 1) |
| 6 | 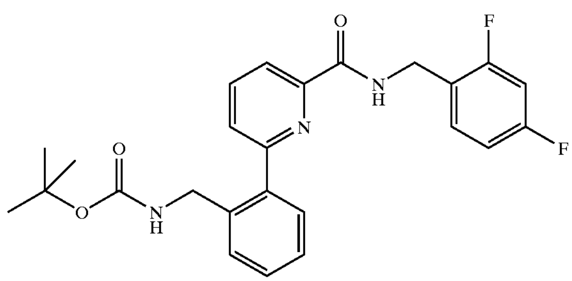 | 454 (M + 1) |
| 7 | 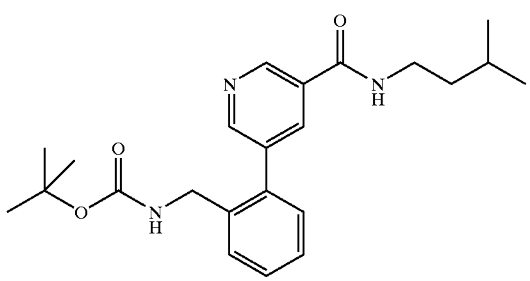 | 398 (M + 1) |
| 8 | 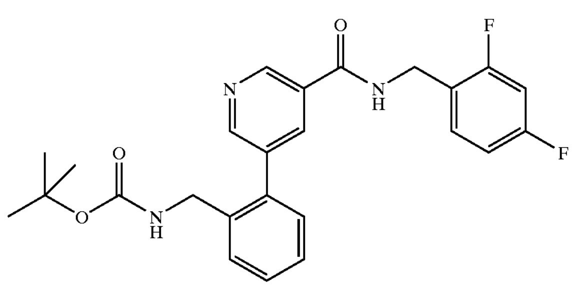 | 454 (M + 1) |

Hydrolysis of the Bisaryls VIII to the Acids of the Formula IX (Scheme 2)

General Working Procedure 1 eq. of the ester VIII was dissolved in methanol/THF (3/1, 5 ml/mmol) and treated with 2 eq. of a 1 molar LiOH solution and stirred at room temperature overnight. The solution was then diluted with water and adjusted to pH 3–4 using KHSO$_4$ solution. It was extracted a number of times with dichloromethane, and the organic phase was dried and concentrated. Yields of between 90 and 95% are typically obtained.

The compound of the formula IX below was prepared according to this procedure:

| Compound | Structure | Mass (ES+): m/z = |
|---|---|---|
| 14 | 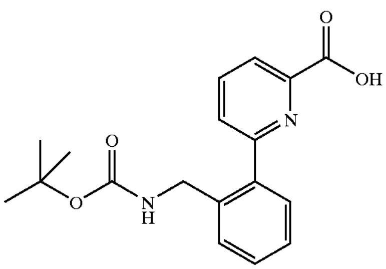 | 329 (M + 1), 229 (M − 99) |

Synthesis of the Amides IV by Amide Coupling to the Acids IX (Scheme 2)

General Working Procedure for the Amide Coupling 1 eq. of acid IX was dissolved in dichloromethane (20 ml/mmol) and treated with 2 eq. of triethylamine, 1.2 eq. of EDC, 0.2 eq. of DMAP and 1.2 eq. of the corresponding amine NH(R3)(R4) and stirred at room temperature overnight. The reaction solution was washed with water and purified by RP-HPLC. Basic compounds were isolated as trifluoroacetates.

A number of examples were synthesized according to this procedure:

| Example | Structure | Mass (ES+): m/z = |
|---|---|---|
| 9 | 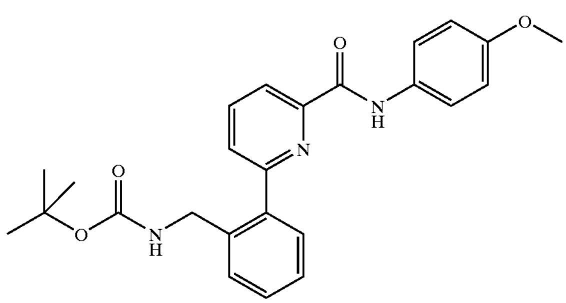 | 434 (M + 1) |
| 10 | 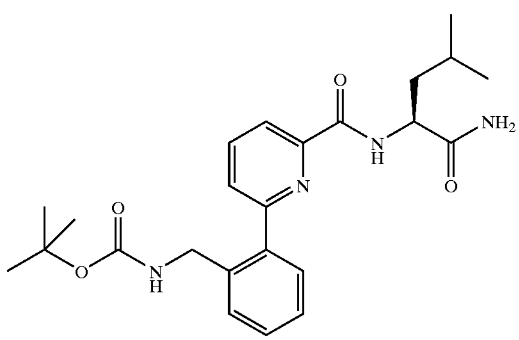 | |
| 11 | 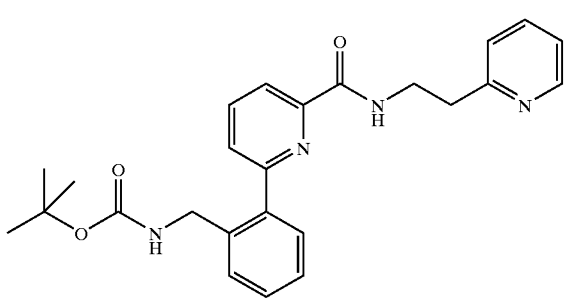 | |

Removal of the Boc Protective Group to Give the Amines V (Schemes 1 and 2)

General Working Procedure 1 eq. of the N-Boc compound is dissolved in dichloromethane/trifluoroacetic acid (3/1, 10 ml/mmol) and stirred at room temperature for 3 h. The mixture is then concentrated on a rotary evaporator and the residue is coevaporated with toluene. The amines V are used for further reactions without further purification. All compounds were characterized by mass spectrometry.

Reactions of the Amines V with Various Reagents to Give the Compounds I According to the Invention General Working Procedure for the Reaction to Give Carbamates of the Formula I 1 eq. of the amine is dissolved in dichloromethane (about 10 ml/mmol) and treated with 1.2 eq. (2.2 eq. when using the trifluoroacetate) of triethylamine and 1.2 eq. of the succinimidyl carbonate (or alternatively of the corresponding chloroformate) and stirred overnight. The mixture is diluted with dichloromethane and washed with NaHCO$_3$ solution. The organic phase is dried, concentrated and, if necessary, purified by RP-HPLC.

EXAMPLE 12
(S)-1-(Phenylethyl){2-[6-(2-pyridin-2-ylethylcarbamoyl)pyridin-2-yl]benzyl}carbamate

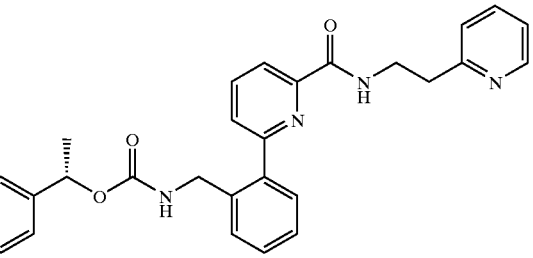

20 mg (0.06 mmol) of 6-(2-aminomethylphenyl)pyridine-2-carboxylic acid (2-pyridin-2-ylethyl)amide were dissolved in 3 ml of dry dichloromethane, and treated with 7 mg (0.07 mmol) of triethylamine and 18 mg (0.17 mmol) of (S)-2-phenylethyloxy-carbonyloxysuccinimide. After a reaction time of 18 h, the mixture was diluted with 15 ml of dichloromethane, washed with saturated NaHCO$_3$ solution and the organic phase was dried and concentrated. After purification by RP-HPLC, 12 mg (28%) of a colorless substance were obtained in the form of its bis (trifluoroacetate).

MS (ES+): m/z=481 (M+1).
$^1$H-NMR (CDCl$_3$): δ=8.60 (1H, m), 8.05-7.86 (3H, m), 7.58-7.29 (13H, m), 5.75 (1H, q, J=6.6 Hz), 5.65 (1H, br s), 4.22 (2H, m), 3.93 (2H, t, J=4.9 Hz), 3.84 (2H, m), 1.48 (3H, d, J=6.6 Hz).

Further examples which were prepared according to the working procedure:

| Example | Structure | Mass (ES+): m/z = |
|---|---|---|
| 13 | 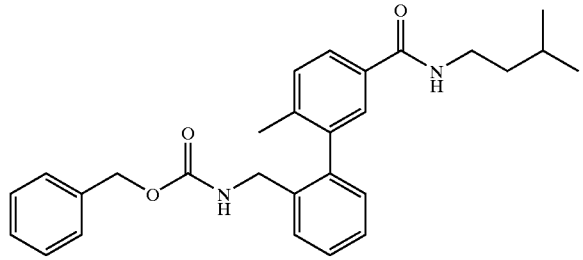 | 445 (M + 1) |
| 14 | 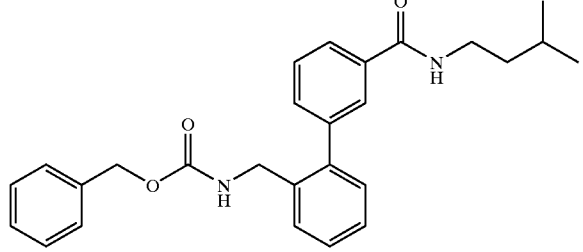 | 431 (M + 1) |

-continued

| Example | Structure | Mass (ES+): m/z = |
|---------|-----------|-------------------|
| 15 | 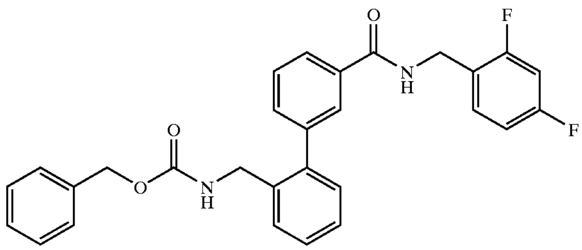 | 487 (M + 1) |
| 16 | 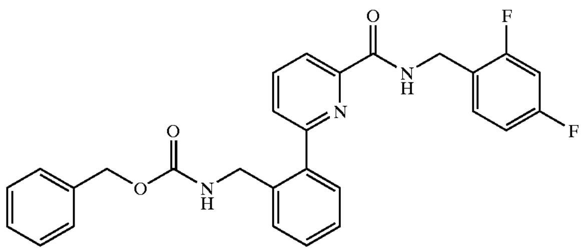 | 488 (M + 1) |
| 17 | 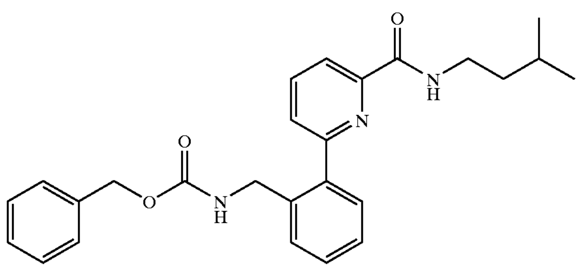 | 432 (M + 1) |
| 18 | 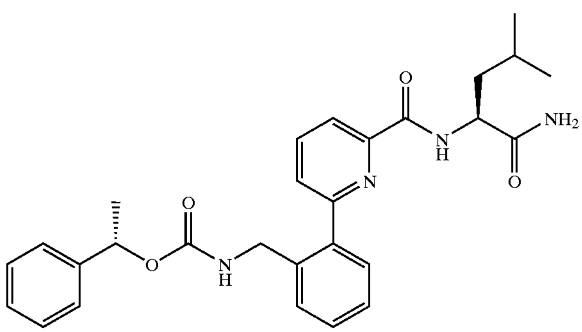 | 489 (M + 1) |
| 19 | 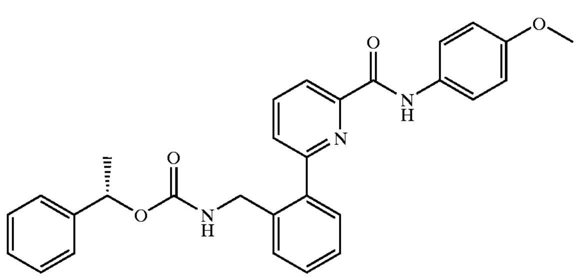 | 482 (M + 1) |

General Procedure for the Reaction to Give Amides of the Formula I

A) 1 eq. of the amine V is dissolved in dichloromethane (about 10 ml/mmol), treated with 1.2 eq. (2.2 eq. when using the trifluoroacetate) of diisopropylethylamine and 1.2 eq. of the acid chloride and stirred overnight. The mixture is diluted with dichloromethane and washed with NaHCO₃ solution. The organic phase is dried, concentrated and, if necessary, purified by RP-HPLC.

B) 1 eq. of the amine V is dissolved in dichloromethane (about 10 ml/mmol), treated with 1.2 eq (2.2 eq. when using the trifluoroacetate) of diisopropylethylamine, treated with 1.2 eq. of the acid and 1.2 eq. of TFFH and stirred overnight. The mixture is diluted with dichloromethane and washed

EXAMPLE 20

6-(2-{[2-(4-Methoxyphenyl)acetylamino]methyl}phenyl)pyridine-2-carboxylic acid (4-methoxyphenyl)amide

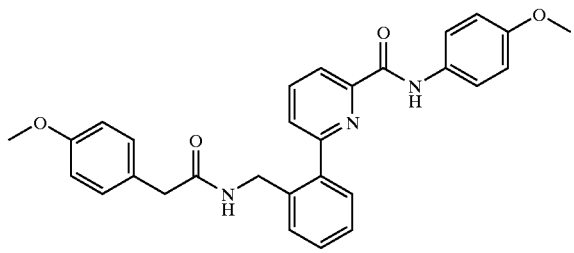

39 mg (0.12 mmol) of 6-(2-Aminomethylphenyl)-pyridine-2-carboxylic acid-(4-methoxyphenyl)-amide were dissolved in 3 ml of dichloromethane, treated with 27 μl (0.144 mmol) of 4-methoxyphenylacetyl chloride and 19 mg (0.144 mmol) of DIPEA and the mixture was stirred overnight. It was diluted with 20 ml of dichloromethane and washed with an NaHCO$_3$ solution. The organic phase was dried, concentrated and purified by RP-HPLC. 56 mg (78%) of the compound of Example 20 were obtained in the form of its trifluoroacetate.

MS (ES+): m/z=482 (M+1).

$^1$H-NMR (CDCl$_3$): δ=9.77 (1H, br s), 8.23 (1H, d, J=7.7 Hz), 7.94 (1H, t, J=7.7 Hz), 7.54 (1H, d, J=7.7 Hz), 7.45–7.36 and 7.09–6.76 (12H, m), 3.81 (3H, s), 3.79 (3H, s), 3.64 (2H, s), 3.42 (2H, s).

Further examples according to general working procedure A or B:

| Example | Structure | Mass (ES+): m/z = |
|---|---|---|
| 21 | 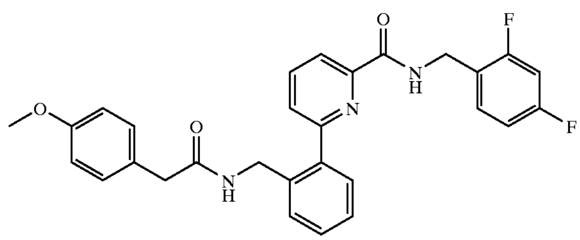 | 502 (M + 1) |
| 22 | 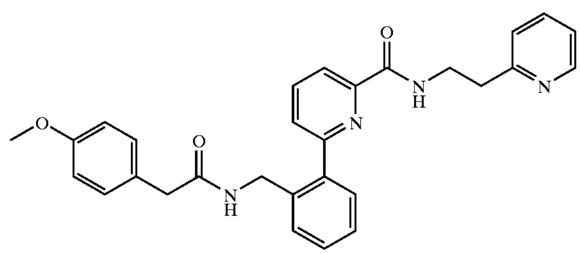 | 481 (M + 1) |
| 23 | 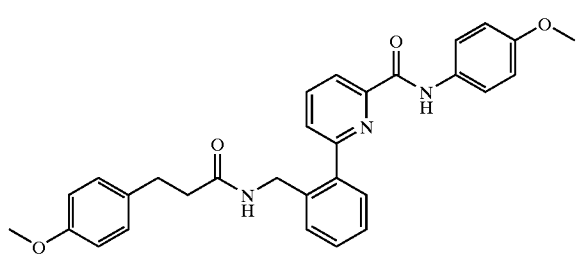 | 496 (M + 1) |
| 24 | 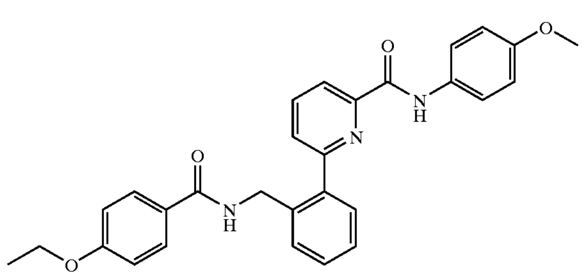 | 482 (M + 1) |

-continued

| Example | Structure | Mass (ES+): m/z = |
|---|---|---|
| 25 | 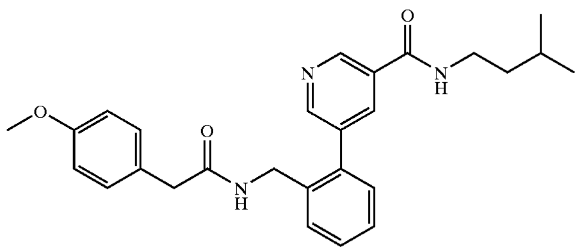 | 462 (M + 1) |
| 26 | 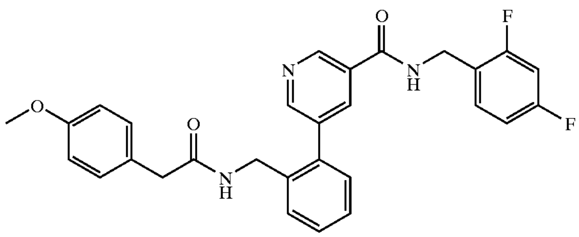 | 502 (M + 1) |
| 27 | 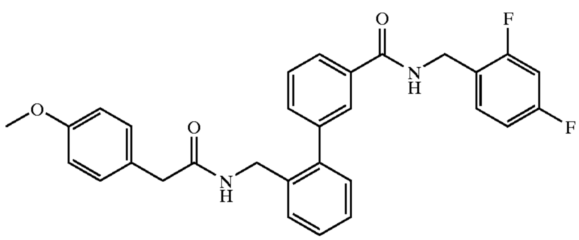 | 501 (M + 1) |
| 28 | 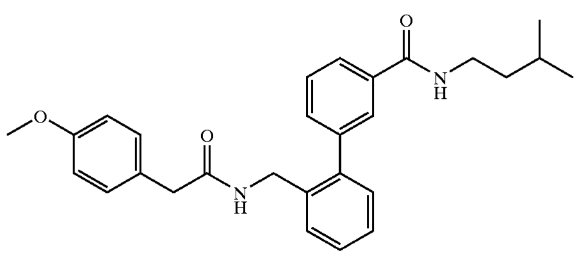 | 445 (M + 1) |
| 29 | 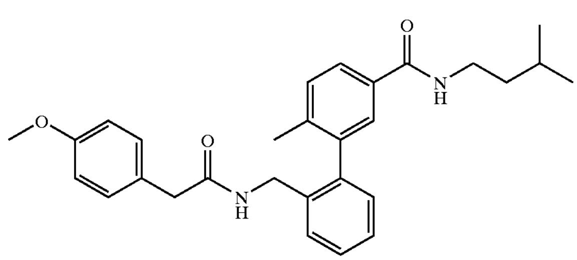 | 459 (M + 1) |
| 30 | 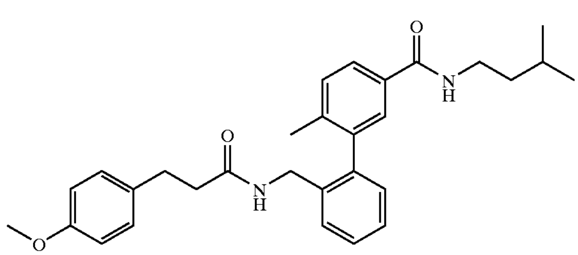 | 473 (M + 1) |

Pharmacological Investigations

Kv1.5 channels from humans were expressed in Xenopus oocytes. To this end, oocytes from *Xenopus laevis* were first isolated and defolliculated. RNA coding for Kv1.5 synthesized in vitro was then injected into these oocytes. After a Kv1.5 protein expression for 1–7 days, Kv1.5 currents were measured on the oocytes using the 2-microelectrode voltage clamp technique. The Kv1.5 channels were in this case as a rule activated using voltage jumps to 0 mV and 40 mV lasting 500 ms. The bath was rinsed using a solution of the following composition: NaCl 96 mM, KCl 2 mM, $CaCl_2$ 1.8 mM, $MgCl_2$ 1 mM, HEPES 5 mM (titrated with NaOH to pH 7.4). These experiments were carried out at room temperature. The following were employed for data acquisition and analysis: Gene clamp amplifier (Axon Instruments, Foster City, USA) and MacLab D/A converter and software (ADInstruments, Castle Hill, Australia). The substances according to the invention were tested by adding them to the bath solution in different concentrations. The effects of the substances were calculated as the percentage inhibition of the Kv1.5 control current which was obtained when no substance was added to the solution. The data were then extrapolated using the Hill equation in order to determine the inhibition concentrations $IC_{50}$ for the respective substances.

In this manner, the following $IC_{50}$ values were determined for the compounds mentioned below:

| Example | $IC_{50}$ [μM] | Example | $IC_{50}$ [μM] | Example | $IC_{50}$ [μM] | Example | $IC_{50}$ [μM] |
|---|---|---|---|---|---|---|---|
| 1 | 6.7 | 2 | <100 | 3 | <100 | 4 | 6.1 |
| 5 | 6 | 6 | <100 | 7 | <100 | 8 | <100 |
| 9 | 3 | 10 | <100 | 11 | 10 | 12 | 2.2 |
| 13 | 7 | 14 | <100 | 15 | <100 | 16 | <100 |
| 17 | <100 | 18 | 4.2 | 19 | 2 | 20 | <100 |
| 21 | 5.7 | 22 | <100 | 23 | <100 | 24 | <100 |
| 25 | <100 | 26 | 7.4 | 27 | 6 | 28 | 4.2 |
| 29 | 4 | 30 | 3.1 | | | | |

We claim:
1. A compound of the formula I,

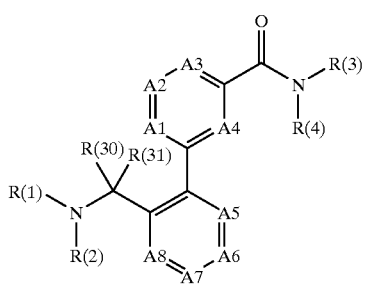

in which:
A1, A2, A3, A4, A5, A6, A7 and A8
  independently of one another are chosen from CH and CR(5);
R(1) is C(O)OR(9), $SO_2R(10)$, COR(11), C(O)NR(12)R(13) or C(S)NR(12)R(13);
  wherein R(9), R(10), R(11) and R(12)
    independently of one another are chosen from $C_xH_{2x}$—R(14);
    where x is 0, 1, 2, 3 or 4, and
    x cannot be 0 if R(14) is OR(15) or $SO_2Me$;

R(14) is alkyl having 1, 2, 3, 4, 5 or 6 atoms, cycloalkyl having 3, 4, 5, 6, 7, 8, 9, 10 or 11 carbon sioms, $CF_3$, $C_2F_5$, $C_3F_7$, $CH_2F$, $CHF_2$, OR(15), $SO_2Me$, substituted or unsubstituted phenyl, substituted or unsubstituted naphthyl, substituted or unsubstituted biphenylyl, substituted or unsubstituted furyl, substituted or unsubstituted thienyl or a substituted or unsubstituted N-containing heteroaromatic having 1, 2, 3, 4, 5, 6, 7, 8 or 9 carbon atoms,
  where the substituted phenyl, substituted naphthyl, substituted biphenylyl, substituted furyl, substituted thienyl and the substituted N-containing heteroaromatic are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, aulfamoyl, methylsulfonyl and methylsulfonylamino;
R(15) is alkyl having 1, 2, 3, 4 or 5 carbon atoms, cycloalkyl having 3, 4, 5 or 6 carbon atoms, $CF_3$, substituted phenyl or unsubstituted phenyl,
  wherein the substituted phenyl is substituted by 1, 2 or 3 substituents chosen from F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino; and
R(13) is hydrogen, alkyl having 1, 2, 3 or 4 carbon atoms or $CF_3$;
R(2) is hydrogen, alkyl having 1, 2, 3 or 4 carbon atoms or $CF_3$;
R(3) is $C_yH_{2y}$—R(16);
  where y is 0, 1, 2, 3 or 4, and
  y cannot be 0 if R(16) is OR(17) or $SO_2Me$;
  R(16) is alkyl having 1, 2, 3, 4, 5 or 6 carbon atoms, cycloalkyl having 3, 4, 5, 6, 7, 8, 9, 10 or 11 carbon atoms, $CF_3$, $C_2F_5$, $C_3F_7$, $CH_2F$, $CHF_2$, OR(17), $SO_2Me$, substituted or unsubstituted phenyl, substituted or unsubstituted naphthyl, substituted or unsubstituted furyl, substituted or unsubstituted thienyl or a substituted or unsubstituted N-containing heteroaromatic having 1, 2, 3, 4, 5, 6, 7, 8 or 9 carbon atoms,
    where the substituted phenyl, substituted naphthyl, substituted furyl, substituted thienyl and the substituted N-containing heteroaromatic are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino; and
  R(17) is hydrogen, alkyl having 1, 2, 3, 4 or 5 carbon atoms, cycloalkyl having 3, 4, 5 or 6 carbon atoms, $CF_3$, substituted phenyl, unsubstituted phenyl, substituted 2-, 3- or 4-pyridyl, or unsubstituted 2-, 3- or 4-pyridyl,
    where the substituted phenyl and substituted 2-, 3- or 4-pyridyl are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

or
- R(3) is CHR(18)R(19);
    - where R(18) is hydrogen or $C_zH_{2z}$—R(16), where R(16) is defined as indicated above;
    - z is 0, 1, 2 or 3;
    - R(19) is COOH, CONH$_2$, CONR(20)R(21), COOR(22) or CH$_2$OH;
    - R(20) is hydrogen, alkyl having 1, 2, 3, 4 or 5 carbon atoms, $C_vH_{2v}$—CF$_3$, substituted $C_wH_{2w}$-phenyl or unsubstituted $C_wH_{2w}$-phenyl,
        - where the phenyl ring of the substituted $C_wH_{2w}$-phenyl is substituted by 1, 2 or 3 substituents chosen from F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
        - v is 0, 1, 2 or 3;
        - w is 0, 1, 2 or 3;
    - R(21) is hydrogen or alkyl having 1, 2, 3, 4 or 5 carbon atoms; and
    - R(22) is alkyl having 1, 2, 3, 4 or 5 carbon atoms;
- R(4) is hydrogen, alkyl having 1, 2, 3, 4, 5 or 6 carbon atoms or CF$_3$;

or
- R(3) and R(4)
    - together are a chain of 4 or 5 methylene groups, of which one methylene group can be replaced by —O—, —S—, —NH—, —N(methyl)- or —N(benzyl)-;
- R(5) is F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino, where in the case that more than one of the radicals A1 to A8 have the meaning CR(5), the radicals R(5) are defined independently of one another;
- R(30) and R(31)
    - independently of one another are hydrogen or alkyl having 1, 2 or 3 carbon atoms;

or
- R(30) and R(31)
    - together are a chain of 2 methylene groups or a pharmaceutically tolerable salt thereof, in any stereoisomeric form, or a mixture of any such compounds in any ratio.

2. The compound as claimed in claim 1, in which:
- A1, A2, A3, A4, A5, A6, A7 and A8 independently of one another are chosen from CH or CR(5);
- R(1) is C(O)OR(9), SO$_2$R(10), COR(11) or C(O)NR(12)R(13)
    - where R(9), R(10), R(11) and R(12)
        - independently of one another are $C_xH_{2x}$—R(14);
    - where x is 0, 1, 2, 3 or 4; and
        - x cannot be 0 if R(14) is OR(15);
    - R(14) is alkyl having 1, 2, 3 or 4 carbon atoms, cycloalkyl having 3, 4, 5, 6, 7, 8 or 9 carbon atoms, CF$_3$, OR(15), substituted or unsubstituted phenyl, substituted or unsubstituted naphthyl, substituted or unsubstituted biphenylyl, substituted or unsubstituted furyl, substituted or unsubstituted thienyl or a substituted or unsubstituted N-containing heteroaromatic having 1, 2, 3, 4, 5, 6, 7, 8 or 9 carbon atoms,
        - where substituted phenyl, substituted naphthyl, substituted biphenylyl, substituted furyl, substituted thienyl and the substituted N-containing heteroaromatic are each independently substituted by 1, 2 or 3 substituents chosen from F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
    - R(15) is alkyl having 1, 2, 3, 4 or 5 carbon atoms, cycloalkyl having 3, 4, 5 or 6 carbon atoms, CF$_3$, substituted phenyl or unsubstituted phenyl,
        - wherein the substituted phenyl is substituted by 1, 2 or 3 substituents chosen from F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
    - R(13) is hydrogen, alkyl having 1, 2, 3 or 4 carbon atoms or CF$_3$;
- R(2) is hydrogen, alkyl having 1, 2, 3 or 4 carbon atoms or CF$_3$;
- R(3) is $C_yH_{2y}$—R(16);
    - where y is 0, 1, 2, 3 or 4, and
        - y cannot be 0 if R(16) is OR(17) or SO$_2$Me;
    - R(16) is alkyl having 1, 2, 3, 4, 5 or 6 carbon atoms, cycloalkyl having 3, 4, 5, 6, 7, 8, 9, carbon atoms, CF$_3$, OR(17), SO$_2$Me, substituted or unsubstituted phenyl, substituted or unsubstituted naphthyl, substituted or unsubstituted furyl, substituted or unsubstituted thienyl or a substituted or unsubstituted N-containing heteroaromatic having 1, 2, 3, 4, 5, 6, 7, 8 or 9 carbon atoms,
        - where the substituted phenyl, substituted naphthyl, substituted furyl, substituted thienyl and the substituted N-containing heteroaromatic are each independently substituted by 1, 2 or 3 substituents chosen from F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
    - R(17) is hydrogen, alkyl having 1, 2, 3, 4 or 5 carbon atoms, cycloalkyl having 3, 4, 5 or 6 carbon atoms, CF$_3$, substituted phenyl, unsubstituted phenyl, substituted 2-, 3- or 4-pyridyl, or unsubstituted 2-, 3- or 4-pyridyl
        - where the substituted phenyl or substituted 2-, 3- or 4-pyridyl are each independently substituted by 1, 2 or 3 substituents chosen from F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

or
- R(3) is CHR(18)R(19);
    - where R(18) is hydrogen or $C_zH_{2z}$—R(16), where R(16) is defined as indicated above;
    - z is 0, 1, 2 or 3;
    - R(19) is CONH$_2$, CONR(20)R(21), COOR(22) or CH$_2$OH;
    - R(20) is hydrogen, alkyl having 1, 2, 3, 4 or 5 carbon atoms, $C_vH_{2v}$—CF$_3$, substituted $C_wH_{2w}$-phenyl, or substituted $C_wH_{2w}$-phenyl,
        - where the phenyl ring of the substituted $C_wH_{2w}$-phenyl is substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

v is 0, 1, 2 or 3;

w is 0, 1, 2 or 3;

R(21) is hydrogen or alkyl having 1, 2, 3, 4 or 5 carbon atoms; and

R(22) is alkyl having 1, 2, 3, 4 or 5 carbon atoms;

R(4) is hydrogen, alkyl having 1, 2, 3, 4, 5 or 6 carbon atoms or $CF_3$;

R(5) is F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino;

R(30) and R(31)
  independently of one another are hydrogen or alkyl having 1, 2 or 3 carbon atoms;

or

R(30) and R(31)
  are a chain of 2 methylene groups or a pharmaceutically tolerable salt thereof, in any stereoisomeric form, or a mixture of any such compounds in any ratio.

3. The compound as claimed in claim 1, wherein:

A1, A2, A3, A4, A5, A6, A7 and A8 independently of one another are chosen from CH or CR(5);

R(1) is C(O)OR(9), $SO_2R(10)$, COR(11) or C(O)NR(12)R(13);

R(9), R(10), R(11) and R(12)
  independently of one another are $C_xH_{2x}$—R(14);
  where x is 0, 1, 2, 3 or 4, and
    x cannot be 0 if R(14) is OR(15);

R(14) is alkyl having 1, 2, 3, 4, 5 or 6 carbon atoms, cycloalkyl having 3, 4, 5, 6, 7, 8, 9, 10 or 11 carbon atoms, $CF_3$, $C_2F_5$, $C_3F_7$, $CH_2F$, $CHF_2$, OR(15), substituted or unsubstituted phenyl, substituted or unsubstituted naphthyl, substituted or unsubstituted biphenylyl, substituted or unsubstituted furyl, substituted or unsubstituted thienyl or a substituted or unsubstituted N-containing heteroaromatic having 1, 2, 3, 4, 5, 6, 7, 8 or 9 carbon atoms;
  where the substituted phenyl, substituted naphthyl, substituted biphenylyl, substituted furyl, substituted thienyl and the substituted N-containing heteroaromatic are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(15) is alkyl having 1, 2, 3, 4 or 5 carbon atoms, cycloalkyl having 3, 4, 5 or 6 carbon atoms, $CF_3$, substituted phenyl or unsubstituted phenyl,
  wherein the substituted phenyl is substituted by 1, 2 or 3 substituents chosen from F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(13) is hydrogen

R(2) is hydrogen or alkyl having 1, 2 or 3 carbon atoms;

R(3) is CHR(18)R(19);

R(18) is hydrogen or $C_zH_{2z}$—R(16);

R(16) is alkyl having 1, 2, 3, 4, 5 or 6 carbon atoms, cycloalkyl having 3, 4, 5, 6, 7, 8, 9, 10 or 11 carbon atoms, $CF_3$, $C_2F_5$, $C_3F_7$, $CH_2F$, $CHF_2$, OR(17), $SO_2Me$, substituted or unsubstituted phenyl, substituted or unsubstituted naphthyl, substituted or unsubstituted furyl, substituted or unsubstituted thienyl or a substituted or unsubstituted N-containing heteroatom having 1, 2, 3, 4, 5, 6, 7, 8 or 9 carbon atoms,
  where the substituted phenyl, substituted naphthyl, substituted furyl, substituted thienyl and the substituted N-containing heteroaromatic are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

z is 0, 1, 2 or 3;

R(19) is $CONH_2$, CONR(20)R(21), COOR(22) or $CH_2OH$;

R(20) is hydrogen, alkyl having 1, 2, 3, 4 or 5 carbon atoms, $C_vH_{2v}$—$CF_3$, substituted $C_wH_{2w}$-phenyl, or unsubstituted $C_wH_{2w}$-phenyl
  where the phenyl ring of the substituted $C_wH_{2w}$-phenyl is substituted by 1, 2 or 3 substituents chosen from F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

v is 0, 1, 2 or 3;

w is 0, 1, 2 or 3;

R(21) is hydrogen or alkyl having 1, 2, 3, 4 or 5 carbon atoms;

R(22) is alkyl having 1, 2, 3, 4 or 5 carbon atoms;

R(4) is hydrogen or alkyl having 1 or 2 carbon atoms;

R(5) is F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino;

R(30) and R(31)
  independently of one another are hydrogen or methyl or a pharmaceutically tolerable salt thereof, in any stereoisomeric form, or a mixture of any such compounds in any ratio.

4. The compound as claimed in claim 1, wherein:

A1, A2, A3, A4, A5, A6, A7 and A8
  independently of one another are chosen from CH or CR(5);

R(1) is C(O)OR(9), $SO_2R(10)$, COR(11) or C(O)NR(12)R(13);

where R(9), R(10), R(11) and R(12)
  independently of one another are $C_xH_{2x}$—R(14);
  where x is 0, 1, 2, 3 or 4;

R(14)
  is alkyl having 1, 2, 3, 4 carbon atoms, cycloalkyl having 3, 4, 5, 6, 7, 8, or 9 carbon atoms, $CF_3$, substituted or unsubstituted phenyl, substituted or unsubstituted naphthyl, substituted or unsubstituted biphenylyl, substituted or unsubstituted furyl, substituted or unsubstituted thienyl or a substituted or unsubstituted N-containing heteroaromatic having 1, 2, 3, 4, 5, 6, 7, 8 or 9 carbon atoms;
  where the substituted phenyl, substituted naphthyl, substituted biphenylyl, substituted furyl, substituted thienyl and the substituted N-containing heteroaromatic are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(13) is hydrogen;
R(2) is hydrogen or methyl;
R(3) is $C_yH_{2y}$—R(16);
  where y is 0, 1, 2, 3 or 4; and
  y cannot be 0 if R(16) is OR(17);
  R(16) is alkyl having 1, 2, 3, 4, 5 or 6 carbon atoms, cycloalkyl having 3, 4, 5, 6, 7, 8, 9 carbon atoms, $CF_3$, OR(17), $SO_2Me$, substituted or unsubstituted phenyl, substituted or unsubstituted naphthyl, substituted or unsubstituted furyl, substituted or unsubstituted thienyl or a substituted or unsubstituted N-containing heteroatom having 1, 2, 3, 4, 5, 6, 7, 8 or 9 carbon atoms,
    where the substituted phenyl, substituted naphthyl, substituted furyl, substituted thienyl and the substituted N-containing heteroaromatic are each independently substituted by 1, 2 or 3 substituents chosen from F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
  R(17) is hydrogen, alkyl having 1, 2, 3, 4 or 5 carbon atoms, cycloakyl having 3, 4, 5 or 6 carbon atoms, $CF_3$, substituted phenyl, unsubstituted phenyl, substituted 2-, 3-, or 4-pyridyl, or unsubstituted 2-, 3- or 4-pyridyl
    where the substituted phenyl or substituted 2-, 3- or 4-pyridyl are each indepedently substituted by 1, 2 or 3 substituents chosen from F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(4) is hydrogen or alkyl having 1 or 2 carbon atoms;
R(5) is F, Cl, Br, I, $CF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino;
R(30) and R(31)
  independently of one another are hydrogen or methyl;
or a pharmaceutically tolerable salt thereof, in any stereoisomeric form, or a mixture of any such compounds in any ratio.

5. The compound as claimed in claim 4, wherein:
A4 is CH;
A1, A2, A3, A4, A5, A6, A7 and A8
  independently of one another are chosen from nitrogen, CH or CR(5), where at least 5 of these groups are CH or a pharmaceutically tolerable salt thereof, in any stereoisomeric form, or a mixture of any such compounds in any ratio.

6. The compound as claimed in claim 5, wherein:
R(1) is C(O)OR(9), $SO_2R$(10), COR(11) or C(O)NR(12)R(13);
  where R(9), R(10), R(12) and R(12)
    independently of one another are $C_xH_{2x}$—R(14);
    where x is 0, 1, 2 or 3;
    R(14) is alkyl having 1, 2, 3 or 4 carbon atoms, cycloalkyl having 3, 4, 5, 6, 7, 8 or 9 carbon atoms, $CF_3$, substituted phenyl, unsubstituted phenyl, substituted pyridyl, or unsubstituted pyridyl
      where the substituted phenyl and substituted pyridyl are each independently substituted by 1 or 2 substituents chosen from F, Cl, Br, I, $CF_3$, $OCF_3$, OH, alkyl having 1, 2 or 3 carbon atoms or alkoxy having 1 or 2 carbon atoms;
  R(13) is hydrogen;
R(2) is hydrogen;
R(3) is $C_yH_{2y}$—R(16),
  y is 0, 1 or 2;
  R(16) is alkyl having 1, 2, 3 carbon atoms, cycloalkyl having 5 or 6 carbon atoms, $CF_3$, substituted phenyl, unsubstituted phenyl, substituted pyridyl, or unsubstituted pyridyl
    where the substituted phenyl and substituted pyridyl are each independently substituted by 1 or 2 substituents chosen from F, Cl, $CF_3$, alkyl having 1, 2 or 3 carbon atoms and alkoxy having 1 or 2 carbon atoms;
R(4) is hydrogen;
R(5) is F, Cl, $CF_3$, CN, COOMe, $CONH_2$, COMe, $NH_2$, OH, alkyl having 1, 2 or 3 carbon atoms or alkoxy having 1 or 2 carbon atoms;
R(30) and R(31)
  independently of one another are hydrogen or methyl;
or a pharmaceutically tolerable salt thereof, in any stereoisomeric form, or a mixture of any such compounds in any ratio.

7. The compound as claimed in claim 6, wherein:
R(1) is C(O)OR(9) or COR(11);
  where R(9) and R(11)
    independently of one another are $C_xH_{2x}$—R(14);
    where x is 0, 1, 2 or 3;
    R(14) is cycloalkyl having 5 or 6 carbon atoms, substituted phenyl, or unsubstituted phenyl
      where the substituted phenyl is substituted by 1 or 2 substituents chosen from F, Cl, Br, I, $CF_3$, $OCF_3$, OH, alkyl having 1, 2 or 3 carbon atoms or alkoxy having 1 or 2 carbon atoms;
R(2) is hydrogen;
R(3) is $C_yH_{2y}$—R(16);
  y is 0, 1 or 2;
  R(16) is alkyl having 1, 2 or 3 carbon atoms, cycloalkyl having 5 or 6 carbon atoms, substituted phenyl, unsubstituted phenyl, substituted pyridyl, or unsubstituted pyridyl,
    where the substituted phenyl and substituted pyridyl are each independently substituted by 1 or 2 substituents chosen from F, Cl, $CF_3$, $OCF_3$, alkyl having 1, 2 or 3 carbon atoms and alkoxy having 1 or 2 carbon atoms;
R(4) is hydrogen;

R(5) is F, Cl, alkyl having 1, 2 or 3 carbon atoms or alkoxy having 1 or 2 carbon atoms;

R(30) and R(31)
    are hydrogen or a pharmaceutically tolerable salt thereof, in any stereoisomeric form, or a mixture of any such compounds in any ratio.

8. A method for treating or preventing a $K^+$ channel-mediated diseases comprising administering to a patient an effective amount of at least one compound chosen from the compounds as claimed in claim 1.

9. A method for treating or preventing cardiac arrhythmias which can be eliminated by action potential prolongation comprising administering to a patient an effective amount of at least one compound chosen from the compounds as claimed in claim 1.

10. A method for treating or preventing reentry arrhythmias comprising administering to a patient an effective amount of at least one compound chosen from the compounds as claimed in claim 1.

11. A method for treating or preventing supraventricular arrhythmias comprising administering to a patient an effective amount of at least one compound chosen from the compounds as claimed in claim 1.

12. A method for treating or preventing atrial fibrillation or atrial flutters comprising administering to a patient an effective amount of at least one compound chosen from the compounds as claimed in claim 1.

13. A method for terminating atrial fibrillation or atrial flutters comprising administering to a patient an effective amount of at least one compound chosen from the compounds as claimed in claim 1.

* * * * *